United States Patent
Colyer

(10) Patent No.: US 10,689,541 B2
(45) Date of Patent: Jun. 23, 2020

(54) COATINGS WITH WAX-MODIFIED HYPERBRANCHED AND FLEXIBLE HYPERBRANCHED POLYOLS

(71) Applicant: BASF COATINGS GMBH, Münster (DE)

(72) Inventor: Emerson Keith Colyer, Whitehouse, OH (US)

(73) Assignee: BASF COATINGS GMBH, Muenster (DE)

(*) Notice: Subject to any disclaimer, the term of this patent is extended or adjusted under 35 U.S.C. 154(b) by 0 days.

(21) Appl. No.: 16/333,779

(22) PCT Filed: Sep. 6, 2017

(86) PCT No.: PCT/EP2017/072336
§ 371 (c)(1),
(2) Date: Mar. 15, 2019

(87) PCT Pub. No.: WO2018/050509
PCT Pub. Date: Mar. 22, 2018

(65) Prior Publication Data
US 2019/0256737 A1 Aug. 22, 2019

Related U.S. Application Data

(63) Continuation of application No. 15/266,159, filed on Sep. 15, 2016, now abandoned.

(51) Int. Cl.
| | | |
|---|---|---|
| C09D 1/02 | (2006.01) | |
| C09D 167/08 | (2006.01) | |
| B05D 1/02 | (2006.01) | |
| B05D 3/02 | (2006.01) | |
| B05D 3/06 | (2006.01) | |
| C09D 167/00 | (2006.01) | |
| C08G 83/00 | (2006.01) | |
| C07C 69/75 | (2006.01) | |
| C09D 201/00 | (2006.01) | |

(52) U.S. Cl.
CPC .......... *C09D 167/08* (2013.01); *B05D 1/02* (2013.01); *B05D 3/0263* (2013.01); *B05D 3/0272* (2013.01); *B05D 3/06* (2013.01); *C07C 69/75* (2013.01); *C08G 83/005* (2013.01); *C08G 83/006* (2013.01); *C09D 167/00* (2013.01); *C09D 201/005* (2013.01); *B05D 2508/00* (2013.01); *C07C 2601/14* (2017.05)

(58) Field of Classification Search
USPC .......................................... 528/271, 272, 279
See application file for complete search history.

(56) References Cited

U.S. PATENT DOCUMENTS

| | | |
|---|---|---|
| 3,001,973 A | 9/1961 | Piepenbrink et al. |
| 3,082,180 A | 3/1963 | Boldizar et al. |
| 3,124,605 A | 3/1964 | Wagner |
| 3,152,162 A | 10/1964 | Fischer et al. |
| 3,201,372 A | 8/1965 | Wagner |
| 3,394,164 A | 7/1968 | McClellan et al. |
| 3,644,457 A | 2/1972 | Klaus et al. |
| 4,105,708 A | 8/1978 | Parekh |
| 4,293,692 A | 10/1981 | Pai et al. |
| 5,578,675 A | 11/1996 | Mormile et al. |
| 6,515,192 B1 | 2/2003 | Rink et al. |
| 6,569,956 B1 | 5/2003 | Ramesh |
| 6,646,049 B2 | 11/2003 | Ramesh |
| 6,861,150 B2 | 3/2005 | Ramesh et al. |
| 7,226,971 B2 | 6/2007 | Ramesh et al. |
| 7,858,733 B2 | 12/2010 | Bruchmann et al. |
| 9,938,429 B2 | 4/2018 | Colyer et al. |
| 2011/0135832 A1 | 6/2011 | Lane et al. |
| 2013/0136865 A1 | 5/2013 | Groenewolt et al. |
| 2016/0017175 A1 | 1/2016 | Colyer et al. |

FOREIGN PATENT DOCUMENTS

| | | |
|---|---|---|
| BE | 752261 A | 12/1970 |
| BE | 761626 A | 6/1971 |
| DE | 953012 C | 11/1956 |
| DE | 1022789 B | 1/1958 |
| DE | 1027394 B | 4/1958 |
| DE | 1092007 B | 11/1960 |
| DE | 1101394 B | 3/1961 |
| DE | 1222067 B | 8/1966 |
| DE | 1929034 A1 | 12/1970 |
| DE | 2004048 A1 | 12/1970 |
| DE | 2504400 A1 | 8/1976 |
| DE | 2537685 A1 | 3/1977 |
| DE | 2552350 A1 | 5/1977 |
| EP | 0008127 A1 | 2/1980 |

(Continued)

OTHER PUBLICATIONS

Steven R. Meyers et al : "Anionic Amphiphilic Dendrimers as Antibacterial Agents", Journal of the American Chemical Society, vol. 130, No. 44, Nov. 5, 2008 (Nov. 5, 2008), pp. 14444-4445, XP055456351, US ISSN: 0002-7863, DOI: 10.1021/ja806912a, Supplementary Information, reaction scheme, compound 2; p. 4.
International Search Report and Written Opinion for International Patent Application No. PCT/EP2017/072336, dated Mar. 14, 2018, 13 pages.
Culbertson, "Aminoplasts : Amino Resins", Encyclopedia of Polymer Science and Technology, vol. 1, 1985, pp. 725-789.
Scriba G K: "Synthesis and In Vitro Degradation Oftestosterone-Lipid Conjugates", Archiv Der Pharmazie, Wileyverlag, Weinheim, vol. 328, No. 3, Jan. 1, 1995 (Jan. 1, 1995), pp. 271-276, XP001023958, ISSN: 0365-6233, DOI: 10.1002/ARDP.19953280313.

(Continued)

*Primary Examiner* — Terressa Boykin
(74) *Attorney, Agent, or Firm* — Armstrong Teasdale LLP

(57) ABSTRACT

Wax-modified hyperbranched polyols and wax-modified flexible hyperbranched polyols are described, as are coating compositions containing these polyols. These polyols provide excellent coatings, especially matte coatings, and allow for the exclusion of silica in coatings.

13 Claims, No Drawings

(56) References Cited

FOREIGN PATENT DOCUMENTS

| EP | 0249201 A2 | 12/1987 |
|---|---|---|
| EP | 0276501 A2 | 8/1988 |
| EP | 0377177 A1 | 7/1990 |
| GB | 994890 A | 6/1965 |
| NL | 7102524 A | 8/1971 |
| WO | 9422968 A1 | 10/1994 |
| WO | 9712945 A1 | 4/1997 |
| WO | 2018046334 A1 | 3/2018 |
| WO | 2018046335 A1 | 3/2018 |

OTHER PUBLICATIONS

Mohamed Attya et al : "Endogenous lipase catalyzed transesterification ofolive oil fats. The formation of isomeric and oligomeric triacyleglycerols: Formation ofisomeric and oligomeric triglycerides", Journal of Mass Spectrometry, vol. 47, No. 9, Sep. 1, 2012 (Sep. 1, 2012), pp. 1247-1253, XP055456359, GBISSN: 1076-5174, DOI: 10.1002/jms.3029.

COATINGS WITH WAX-MODIFIED HYPERBRANCHED AND FLEXIBLE HYPERBRANCHED POLYOLS

CROSS-REFERENCE TO RELATED APPLICATIONS

This application is a U.S. National Phase Application of International Patent Application No. PCT/EP2017/072336, filed Sep. 6, 2017, which is a continuation of and claims the benefit of priority to U.S. patent application Ser. No. 15/266,159, filed Sep. 15, 2016, the entire contents of which are hereby incorporated by reference herein.

FIELD

Wax-modified hyperbranched polyols and wax-modified flexible hyperbranched polyols are described, as are coating compositions containing these polyols. These polyols provide excellent coatings, especially matte coatings, and allow for the exclusion of silica in coatings.

BACKGROUND

This section provides information helpful in understanding the invention but that is not necessarily prior art. All references discussed below are incorporated herein by reference in their entirety.

Colyer, US 2016/0017175, published Jan. 21, 2016, describes a coating composition that includes a flexible hyperbranched polyol preparable by (a) reacting a polyol comprising at least three hydroxyl groups with an aliphatic dicarboxylic acid having from 6 to 36 carbon atoms or an esterifiable derivative of the aliphatic dicarboxylic acid to form a hydroxyl-functional first intermediate product; (b) reacting the first intermediate product with a cyclic carboxylic acid anhydride to form a carboxylic acid-functional second intermediate product; and (c) reacting the second intermediate product with an epoxide-functional compound having one epoxide group to form the hyperbranched polyol. The coating composition may be cured to a coating layer having excellent flexibility.

Ramesh, U.S. Pat. No. 6,569,956, issued May 27, 2003, discloses a hyperbranched polyester polyol macromolecule having a plurality of both embedded and exterior hydroxyl groups. The hyperbranched polyol includes a central nucleus, a first chain extension, an intermediate substituent and a second chain extension. The central nucleus is a hydrocarbon structure with a plurality of oxygen atoms. The first chain extender is attached to the central nucleus and includes a carboxylic ester group and a plurality of hydroxyl groups. The intermediate substituent is attached to the first chain extender and is a polyfunctional carboxylic acid or anhydride. The preferred intermediate substituent is a cyclic compound. The second chain extension is attached to the intermediate substituent. The preferred second chain extension includes a glycidyl ester or epoxy. Also disclosed are coating compositions in which the lower branched polyol is reacted with an aminoplast or with an isocyanate.

Rink, U.S. Pat. No. 6,515,192, issued Feb. 4, 2003, discloses hyperbranched compounds having a tetrafunctional central group of the general formula $C[-A_q-X-]_m[-A_r-X-]_n[-A_s-X-]_o[-A_t-X-]$, in which m+n+o+p=4, m=an integer from 1 to 3 and n, o and p=0 or an integer from 1 to 3; q,r,s and t=an integer from 1 to 5, where q>r, s and t; $X=-O-$, $-S-$ or $A=-CR2-$; where $R=-H$, F, —Cl, —Br, —CN, —$NO_2$, C1 to C3 alkyl or C1 to C3 haloalkyl or C1 to C3 alkoxy radical or, if q, r, s and/or t=at least 2, a C2 to C4 alkanediyl and/or C2-C4 oxaalkanediyl radical which bridges 2 to 5 carbon atoms, and/or an oxygen atom —O—, which bridges 3 to 5 carbon atoms, of the radical -A-.

Ramesh, U.S. Pat. No. 6,646,049, issued Nov. 11, 2003 discloses a binder for a coating composition with a principal resin polyol in combination with a hyper-branched polyol as a reactive intermediate and at least one crosslinker. The principal resin polyol is at least one of a polyester polyol, a polyether polyol, and a polyacrylate. Hyper-branched polyester polyols may be used as reactive diluents, which will cross-link with isocyanates, isocyanurates, epoxides, anhydrides or their corresponding polyacids and/or aminoplasts to form a binder having particular properties, to help control the rheology of a coating system. The hyperbranched polyol, the principal resin polyol, or both may, optionally, include a carbamate functional group. Coating compositions may be made using the binders together with additional components.

Ramesh et al., U.S. Pat. No. 6,861,150 issued Mar. 1, 2005 discloses a rheology control agent for a coating composition that is the reaction product of a first compound comprising a plurality of hydroxyl groups, of a lactone compound, and of a carbamate compound.

Ramesh et al., U.S. Pat. No. 7,226,971, issued Jun. 5, 2007, discloses a polyester resin for use in a coating composition. The polyester resin is the reaction product of a first compound comprising a plurality of hydroxyl groups, a lactone compound, a carboxylic acid anhydride, an epoxy compound having at least one epoxy group, and a carbamate compound.

Bruchmann et al., U.S. Pat. No. 7,858,733, issued Dec. 28, 2010, discloses high-functionality highly branched or hyperbranched polyesters based on di-, tri- or polycarboxylic acids and di-, tri- or polyols, processes for preparing them, and their use in coatings. The high-functionality highly branched or hyperbranched polyesters have a molecular weight $M_n$ of at least 500 g/mol and a polydispersity $M_w/M_n$ of 1.2-50, obtainable by reacting at least one aliphatic, cycloaliphatic, araliphatic or aromatic dicarboxylic acid (A2) or derivatives thereof and at least one divalent aliphatic, cycloaliphatic, araliphatic, or aromatic alcohol (B2), containing 2 OH groups, with either a) at least one x-valent aliphatic, cycloaliphatic, araliphatic or aromatic alcohol ($C_x$) containing more than two OH groups, x being a number greater than 2, preferably between 3 and 8, particularly preferably between 3 and 6, more preferably from 3 to 4 and in particular 3 or b) at least one aliphatic, cycloaliphatic, araliphatic or aromatic carboxylic acid ($D_y$) or derivatives thereof containing more than two acid groups, y being a number greater than 2, preferably between 3 and 8, more preferably between 3 and 6, very preferably from 3 to 4 and in particular 3, in each case in the presence if appropriate of further functionalized building blocks E and c) subsequently reacting the product, if appropriate, with a monocarboxylic acid F, and the ratio of the reactive groups in the reaction mixture being chosen so as to set a molar ratio of OH groups to carboxyl groups or derivatives thereof of from 5:1 to 1:5, preferably from 4:1 to 1:4, more preferably from 3:1 to 1:3 and very preferably from 2:1 to 1:2.

It remains desirable to make further improvements in coating compositions containing hyperbranched and flexible hyperbranched polyols to provide coating compositions and coatings with excellent properties and which permit the coating composition to be made with a low content of volatile organic compounds.

SUMMARY

Disclosed are wax-modified flexible hyperbranched polyols and wax-modified hyperbranched polyols. Coating compositions and coatings containing these polyols, both as is and as incorporated within other materials, are also described.

Preferred wax-modified flexible hyperbranched polyols are preparable by, for example, (a) reacting a polyol, preferably one comprising at least three hydroxyl groups, with (a') a long-chain, wax-like reactant comprising a carboxylic acid functionality and optionally with (a") an aliphatic dicarboxylic acid having from 6 to 36 carbon atoms or an esterifiable derivative of the aliphatic dicarboxylic acid, to form a hydroxyl-functional first intermediate product; (b) reacting the first intermediate product with a cyclic carboxylic acid anhydride to form a carboxylic acid-functional second intermediate product; and (c) reacting the second intermediate product with an epoxide-functional compound having one epoxide group to form the wax modified flexible hyperbranched polyol. Esterifiable derivatives of the dicarboxylic acid having from 6 to 36 carbon atoms include their anhydrides and esterifiable esters. In a preferred embodiment the polyol is reacted only with a long-chain, wax-like reactant comprising a carboxylic acid functionality in the first step to form the hydroxyl-functional first intermediate product.

Preferred wax-modified hyperbranched polyester polyols are preparable by, for example (a) reacting a polyol, preferably one comprising at least three hydroxyl groups, with (a') a long-chain, wax-like reactant comprising a carboxylic acid functionality and with (a") a first chain extender, which contains a plurality of hydroxyl groups and also contains a carboxyl group, to form a first generation branched core; (b) optionally further reacting the first generation branched core with the first chain extender to form a subsequent generation branched core; (c) reacting the first or subsequent generation branched core with a compound selected from the group consisting of carboxylic anhydrides and acids to form an ester bridge therewith, thereby forming an intermediate polyester macromolecule; and (d) reacting the intermediate polyester macromolecule with a second chain extender having a terminal or non-terminal epoxide group and a branched hydrocarbon chain, to form a wax-modified hyperbranched polyol having both primary and secondary hydroxyl groups thereon.

DETAILED DISCLOSURE

A detailed description of exemplary, nonlimiting embodiments follows.

"A," "an," "the," "at least one," and "one or more" are used interchangeably to indicate that at least one of the item is present; the indefinite articles indicate a plurality of such items may be present unless the context clearly indicates otherwise. All disclosure of ranges includes the endpoints of the ranges and is a disclosure of all values and further divided ranges within the entire range. Each value within a range and the endpoints of a range are hereby all disclosed as separate embodiments. In this description of the invention, for convenience, "polymer" and "resin" are used interchangeably to encompass resins, oligomers, and polymers. The terms "comprises," "comprising," "including," "containing" and "having," are inclusive and therefore specify the presence of stated items, but do not preclude the presence of other items. As used in this specification, the term "or" includes any and all combinations of one or more of the listed items.

Wax-Modified Flexible Hyperbranched Polyols

In an embodiment the wax-modified flexible hyperbranched polyols include:

a) a central nucleus comprising a hydrocarbon structure with a plurality of oxygen atoms;

b) a long-chain wax-like modifier and an optional first flexible extension, both attached to the central nucleus, the long-chain wax-like modifier being formed from a long-chain wax-like reactant comprising a carboxylic acid functionality, the flexible chain extension, if present, being formed from an aliphatic dicarboxylic acid;

c) an intermediate substituent attached to the central nucleus, the intermediate substituent being formed from a compound selected from the group consisting of polyfunctional carboxylic anhydrides and acids thereof, and d) a second chain extension attached to the intermediate substituent and, if present, the optional first flexible extension, the second chain extension comprising a hydroxyl group and being formed from a compound having a terminal or non-terminal epoxide group thereon.

The flexible, hyperbranched polyol can be prepared by a synthesis having a step (a) of reacting a polyol preferably comprising at least three hydroxyl groups with (a') a long-chain, wax-like reactant comprising a carboxylic acid functionality and optionally with (a") an aliphatic dicarboxylic acid having from 6 to 36 carbon atoms or an esterifiable derivative of the aliphatic dicarboxylic acid, to form a hydroxyl-functional first intermediate product.

The polyol may preferably be selected from triols, dimers of triols, tetrols, dimers tetrols, and sugar alcohols. Nonlimiting examples of suitable polyols having three or more hydroxyl groups include glycerol, trimethylolmethane, trimethylolethane, trimethylolpropane, 2,2,3-trimethylolbutane-1,4-diol, 1,2,4-butanetriol, 1,2,6-hexanetriol, tris(hydroxyethyl)amine, tris(hydroxyethyl)amine, tris(hydroxypropyl)amine, erythritol, pentaerythritol, diglycerol, triglycerol or higher condensates of glycerol, di(trimethylolpropane), di(pentaerythritol), pentaerythritol ethoxylate, pentaerythritol propoxylate, trishydroxymethyl isocyanurate, tris(hydroxyethyl) isocyanurate (THEIC), tris(hydroxypropyl) isocyanurate, inositols or sugars, such as glucose, fructose or sucrose, for example, sugar alcohols such as xylitol, sorbitol, mannitol, threitol, erythritol, adonitol (ribitol), arabitol (lyxitol), xylitol, duicitol (galactitol) isomalt, polyetherols with a functionality of three or more, based on alcohols with a functionality of three reacted with ethylene oxide, propylene oxide and/or butylene oxide.

In certain preferred embodiments, the polyol of step (a) is at least one of erythritol, pentaerythritol, dipentaerythritol, trimethylolethane, trimethylolpropane, trimethylolbutane, glycerol, ditrimethylolethane, ditrimethylolpropane, pentaerythritol ethoxylate, and pentaerythriol propoxylate.

The long-chain wax-like reactant comprising a carboxylic acid functionality is not particularly limited. Examples of preferred materials usable as the long-chain wax-like reactant comprising a carboxylic acid include linear and branched, unsubstituted C8-C85, preferably C12-C75, more preferably C14-C60 primary, secondary and tertiary carboxylic acids. Preferred carboxylic acids are unsubstituted linear saturated carboxylic acids. Preferred examples of long-chain wax-like reactants useful herein include the UNICID™ acids available from Baker Hughes, which are long chain, linear primary carboxylic acids with carbon chain lengths from 25 to 50 carbons.

The optional aliphatic dicarboxylic acid having from 6 to 36 carbon atoms or esterifiable derivative of the aliphatic dicarboxylic acid may be linear, branched, or cyclic, with the proviso that cyclic dicarboxylic acids include a noncyclic segment of at least about 6 carbon atoms. Nonlimiting examples of suitable dicarboxylic acids include adipic acid, suberic acid, azelaic acid, sebacic acid, undecanedioic acid (brassylic acid), dodecanedioic acid, traumatic acid, hexadecanedioic acid (thapsic acid), octadecanedioic acid, tetradecanedioic acid, and dimer fatty acids having 36 carbon atoms. In various embodiments, α,ω-dicarboxylic acids and dimer fatty acids having 36 carbon atoms are preferred.

It is known that dimer fatty acids having 36 carbon atoms may have multiple isomers. Dimer fatty acids are commercially available, for example from BASF under the trademark EMPOL®, from Arizona Chemical under the trademark UNIDYME™, from Croda International Plc under the trademark Pripol™, and from Emery Oleochemicals as EMERY® Dimer Acids. Esterifiable derivatives of the dicarboxylic acids having from 6 to 36 carbon atoms include their mono- or diesters with aliphatic alcohols having 1 to 4 carbon atoms, preferably the methyl and ethyl esters, as well as the anhydrides.

Alternately, the optional aliphatic dicarboxylic acid or its derivative may be synthesized in situ prior to the construction of the long-chain wax appended core. This may be accomplished through executing ring-opening reactions of suitable cyclic anhydrides with a diol including oligomeric diols. Non-limiting examples of suitable cyclic anhydrides include Hexahydrophthalic anhydride, Methylhexahydrophthalic anhydride, Succinic anhydride, and Phthalic anhydride. Suitable, non-limiting examples of diols include 1,6-Hexanediol, Polycaprolactone diol, K-Flex UD 320, (a urethane diol available from King Industries), Nonaoxanonacosane-1,29-diol, and Pripol dimer diols available from Croda.

The long-chain wax-like reactant comprising a carboxylic acid functionality and the optional aliphatic dicarboxylic acid having from 6 to 36 carbon atoms (or esterifiable derivative) are reacted with the hydroxyl groups of the polyol. The hydroxyl groups of the polyol can be primary, secondary, and/or tertiary hydroxyl groups.

When the optional aliphatic dicarboxylic acid (or esterifiable derivative) is used, the reaction can occur stepwise, meaning that one or the other of the long-chain wax-like reactant comprising a carboxylic acid and the aliphatic dicarboxylic acid (or esterifiable derivative) is first reacted with the polyol to form a first stage intermediate followed by reaction of the other of the long-chain wax-like reactant comprising a carboxylic acid and the aliphatic dicarboxylic acid (or esterifiable derivative) with the first stage intermediate, or the reaction can take place essentially in one step where both the long-chain wax-like reactant comprising a carboxylic acid and the aliphatic dicarboxylic acid (or esterifiable derivative) are reacted with the polyol essentially simultaneously.

In various examples, the ratio in step (a) of moles of the polyol to moles of the dicarboxylic acid (or esterifiable derivative of the aliphatic dicarboxylic acid) is from about 2.0 to about 2.5, preferably from about 2.0 to about 2.2, and more preferably from about 2.0 to about 2.07 moles of the polyol per mole of the dicarboxylic acid (or esterifiable derivative of the aliphatic dicarboxylic acid). Particularly preferably, on average about one hydroxyl group of each molecule of the invention is reacted with the long-chain wax-like reactant comprising a carboxylic acid in step (a). When the dicarboxylic acid (or esterifiable derivative of the aliphatic dicarboxylic acid) is used, it is also preferable that on average about one hydroxyl group of each polyol molecule is reacted with the dicarboxylic acid (or esterifiable derivative of the aliphatic dicarboxylic acid) in step (a).

The esterification step (a) may be carried out by known, standard methods. For example, this reaction is conventionally carried out at temperatures of between about 180° C. and about 280° C. in the presence, if desired, of an appropriate esterification catalyst. Typical catalysts for the esterification polymerization are protonic acids and Lewis acids, for example sulfuric acid, para-toluenesulfonic acid, sulfates and hydrogen sulfates, such as sodium hydrogen sulfate, phosphoric acid, phosphonic acid, hypophosphorous acid, titanium alkoxides, and dialkyltin oxides, for example dibutyltin oxide, dibutyltin dilaurate, lithium octanoate, under reflux with small quantities of a suitable solvent as entraining agent such as an aromatic hydrocarbon, for example xylene, or a (cyclo)aliphatic hydrocarbon, for example cyclohexane. As a non-limiting, specific example, the polyester may include stannous octoate or dibutyltin oxide. An acidic inorganic, organometallic, or organic catalyst can be used in an amount from 0.1% to 10% by weight, preferably from 0.2% to 2% by weight, based on total weight of the reactants. It may be desirable to carry out the reaction step (a) free of catalyst to avoid or minimize side reactions during subsequent steps.

The esterification of step (a) can be carried out in bulk or in the presence of a solvent that is nonreactive toward the reactants. Nonlimiting examples of suitable solvents include hydrocarbons such as paraffins or aromatics. In some embodiments it may be preferred to use n-heptane, cyclohexane, toluene, ortho-xylene, meta-xylene, para-xylene, xylene isomer mixtures, ethylbenzene, chlorobenzene and ortho- and meta-dichlorobenzene. Other solvents that may be used in the absence of acidic catalysts are ethers, such as dioxane tetrahydrofuran, for example, and ketones such as methyl ethyl ketone and methyl isobutyl ketone, for example. The solvent may be used to aid in removing by-product of the esterification reaction azeotropically.

The amount of solvent that can be used may be at least 0.1% by weight or at least 1% by weight or at least 5% by weight, based on the weight of the starting reactants. Higher amounts of solver may be used, but it is preferred to keep the concentration of reactants high enough to permit the reaction to be carried out in a commercially viable length of time. Examples of ranges of the solvent that may be employed are from 0.1% to about 30% by weight, or from about 1% to about 15% by weight, or from about 5% to about 10% by weight, based in each case on the weight of the starting reactants.

The reaction may be carried out in the presence of a water-removing agent, for example molecular sieves, especially molecular sieve 4 Å, $MgSO_4$ and $Na_2SO_4$.

The reaction(s) of step (a) may be carried out at temperatures of 60° C. to 250° C., for example at temperatures of 100° C. to 240° C. In certain embodiments the reaction(s) of step (a) may be carried out at temperatures of 150° C. to 235° C. The reaction time depends upon known factors, which include temperature, concentration of reactants, and presence and identity of catalyst, if any. Typical reaction times may be from about 1 to about 20 hours.

To minimize final volatile organic content, as much of the solvent used to azeotrope the byproduct from step (a) as is practical may be removed after completion of the reaction of step (a). Small amounts of solvents selected for their performance in the final resin can be used throughout the rest of the synthesis, for example as a flush following a reagent addition. Solvents that can react with anhydrides or epoxides, such as active hydrogen-containing compounds like hydroxy-functional solvents (e.g., alcohols and monoethers of glycols), are preferably avoided during both step (a) and subsequent reaction steps. After step (a), the reaction temperature is preferably kept below at temperature at which condensation-type esterification reactions could take place, for example kept below 150° C., for the remainder of the synthesis to minimize the chance of condensation-type esterification reactions which, at this stage of the synthesis, would have undesirable effects on the molecular weight and architecture. For example, further esterification could produce unwanted branching or an undesirably increased molecular weight. The reaction temperature for steps subsequent to step (a) may be kept below 145° C., below 140° C., or even below 135° C. or 130° C. depending on whether a catalyst is used during step (a) and the nature of any catalyst used.

Optionally, before the hydroxyl-functional first intermediate product prepared in step (a) is reacted with a cyclic carboxylic acid anhydride to form a carboxylic acid-functional second intermediate, the hydroxyl-functional first intermediate can be variably extended through the ring-opening reaction of the intermediate's hydroxyls with a lactone. The number of mols of lactone relative to the mols of the first intermediate will determine the degree of extension away from the core. Non-limiting examples of suitable lactones include ε-Caprolactone, γ-Caprolactone, β-Butyrolactone, β-Propriolactone, γ-Butyrolactone, α-Methyl-γ-butyrolactone, β-Methyl-γ-butyrolactone, γ-Valerolactone, δ-Valerolactone, γ-Decanolactone, δ-Decanolactone, γ-Nonanoic lactone, γ-Octanoic lactone.

The hydroxyl-functional first intermediate product prepared in step (a), or, optionally, an extended derivative thereof, is then reacted with a cyclic carboxylic acid anhydride to form a carboxylic acid-functional second intermediate product. The cyclic carboxylic acid anhydride reacts with at least one of the hydroxyl groups of the hydroxyl-functional first intermediate product to form the second intermediate product having at least one carboxyl group. Preferably, the cyclic carboxylic acid anhydride is reacted with all or substantially all of the hydroxyl groups of the first intermediate product to form the second intermediate product. In a preferred embodiment all the hydroxyl groups of the first intermediate product are present on the polyol. The cyclic carboxylic acid anhydride reacted in step (b) may be either an aromatic or aliphatic cyclic anhydride.

In certain embodiments, the cyclic carboxylic acid anhydride is at least one of maleic anhydride, hexahydrophthalic anhydride, methylhexahydrophthalic anhydride, tetrahydrophthalic anhydride, phthalic anhydride, succinic anhydride, trimellitic anhydride, methyltetrahydrophthalic anhydride, adipic anhydride, glutaric anhydride, malonic anhydride, itaconic acid anhydride, 5-methyl-5-nobornenedicarboxylic acid anhydride, 1,2-cyclohexanedicarboxylic acid anhydride, isatoic acid anhydride, diphenic acid anhydride, substituted anhydrides, particularly including lower-alkyl substituted acid anhydrides such as butylsuccinic acid anhydride, hexylsuccinic acid anhydride, octylsuccinic acid anhydride, butylmaleic acid anhydride, pentylmaleic acid anhydride, hexylmaleic acid anhydride, octylmaleic acid anhydride, butylglutaric acid anhydride, hexylglutaric acid anhydride, heptylglutaric acid anhydride, octylglutaric acid anhydride, alkylcyclohexanedicarboxylic acid anhydrides and alkylphthalic acid anhydrides such as 4-n-butylphthalic acid anhydride, hexylphthalic acid anhydride, and octylphthalic acid anhydride.

In one particular embodiment, the carboxylic acid anhydride comprises hexahydrophthalic anhydride. Hexahydrophthalic anhydride may in some cases be the only carboxylic acid anhydride used in the reaction of step (b).

The reaction of step (b) provides a second intermediate product with a carboxylic acid group for each molecule of cyclic carboxylic acid anhydride reacted with the hydroxyl-functional first intermediate product of step (a), and with a carboxylic group for every molecule of dicarboxylic acid used in step (a). In some example embodiments, the equivalent ratio of the cyclic carboxylic acid anhydride to the first intermediate product is from about 0.8 to about 1.0, preferably from about 0.85 to about 1.0, and more preferably from about 0.9 to about 1.0 equivalents of anhydride groups per equivalent of hydroxyl groups. In one example embodiment, one molecule or substantially one molecule of anhydride reacts with each hydroxyl group of the first intermediate product to form the second intermediate product. In preferred embodiments, substantially all hydroxyl groups of the hydroxyl-functional first intermediate product are reacted with the carboxylic acid anhydride to provide an ester of the hydroxyl group and a carboxylic acid group from opening the cyclic anhydride.

The anhydride ring-opening reaction of step (b) is exothermic. The reaction temperature can be controlled, for example to not exceed about 150° C., by dividing carboxylic acid anhydride reactant addition into two or more added portions. For example, a first added portion may be about one-third to about one-half of the carboxylic acid anhydride and a second portion may be the balance of the carboxylic acid anhydride being reacted in step (b). The temperature of the reaction mixture may be allowed to cool to about 90° C. to 95° C. before each portion is added. After the first portion is added, the reaction mixture may be heated to about 110° C. to 115° C., or higher, resulting in an exotherm that may be allowed to carry the temperature of the reaction mixture upward, but not to exceed the target maximum, for example 150° C. After the exotherm, the reaction mixture may be cooled to about 90° C. to 95° C. for a second anhydride addition. Similarly, after the second anhydride addition has been completed, the reaction mixture may be heated to about 110° C. to 115° C., or higher, after which the reaction exotherm, (and additional heat, if needed), are used to bring the temperature of the reaction mixture up to, for example from about 135° C. to about 145° C. or from about 140° C. to about 145° C., where the reaction mixture is held to allow the reaction to complete.

In a third step (c), from at least about two carboxylic acid groups to all of the carboxylic acid groups of the second intermediate product are reacted with an epoxide-functional compound having one epoxide group to form the wax-modified flexible hyperbranched polyol. Mono-epoxide compounds are well-known in the art, and may be characterized by the general formula:

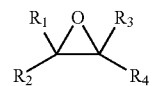

where $R_1$, $R_2$, $R_3$ and $R_4$ are each independently hydrogen or an organic radical, with the proviso that at least one of $R_1$-$R_4$ is other than hydrogen, and may contain unsaturation or heteroatoms or two of $R_1$-$R_4$ may form a cyclic ring, which may contain unsaturation or heteroatoms.

For example, the epoxide-functional compound may be an epoxy ester, also known as a glycidyl ester. Glycidyl esters can be prepared by reacting a monofunctional carboxylic acid with an epihalohydrin (e.g., epichlorohydrin) under conditions well known in the art. Examples of glycidyl esters are glycidyl acetate, glycidyl propionate, glycidyl methyl maleate, glycidyl stearate, glycidyl benzoate, and glycidyl oleate. Among useful glycidyl esters are those having an alkyl group having from 7 to 17 carbon atoms. A particularly preferred glycidyl ester is a glycidyl ester of a saturated synthetic tertiary monocarboxylic acid having 9-11 carbon atoms. In a preferred embodiment, the monofunctional carboxylic acid used to produce the glycidyl esters is a neoalkanoic acid such as, without limitation, neodecanoic or neononanoic acid. Glycidyl esters of neoacids are commercially available, e.g., under the trademark Cardura® from Momentive Specialty Chemicals, Inc., Columbus, Ohio.

Another useful class of monoepoxides is glycidyl ethers. Glycidyl ethers can be prepared by the reaction of monofunctional alcohols (e.g., n-butanol, propanol, 2-ethylhexanol, dodecanol, phenol, cresol, cyclohexanol, benzyl alcohol) with an epihalohydrin (e.g., epichlorohydrin). Useful glycidyl ethers include methyl glycidyl ether, ethyl glycidyl ether, propyl glycidyl ether, butyl glycidyl ether, pentyl glycidyl ether, hexyl glycidyl ether, heptyl glycidyl ether, octyl glycidyl ether, nonyl glycidyl ether, decyl glycidyl ether, undecyl glycidyl ether, dodecyl glycidyl ether, tridecyl glycidyl ether, tetradecyl glycidyl ether, pentadecyl glycidyl ether, hexadecyl glycidyl ether, heptadecyl glycidyl ether, octadecyl glycidyl ether, nonadecyl glycidyl ether, eicosyl glycidyl ether, beneicosyl glycidyl ether, docosyl glycidyl ether, tricosyl glycidyl ether, tetracosyl glycidyl ether, pentacosyl glycidyl ether, decenyl glycidyl ether, undecenyl glycidyl ether, tetradecenyl glycidyl ether, hexadecenyl glycidyl ether, heptadecenyl glycidyl ether, octadecenyl glycidyl ether, nonadecenyl glycidyl ether, eicosenyl glycidyl ether, beneicosenyl glycidyl ether, docosenyl glycidyl ether, tricosenyl glycidyl ether, tetracosenyl glycidyl ether and pentacosenyl glycidyl ether.

The equivalent ratio in step (c) of carboxylic acid groups of the second intermediate product to epoxide groups of the epoxide-functional compound may be from about 1.0 to about 2.5, or from about 1.0 to about 2.0, or from about 1.0 to about 1.5, or from about 1.0 to about 1.3, or from about 1.0 to about 1.1 equivalents of carboxylic acid groups per equivalents epoxide groups. The preferred range of equivalents of carboxylic acid groups to epoxide groups will vary, however, depending on whether the embodiment will be for a solventborne or waterborne coating composition. In one embodiment, the hyperbranched polyol is used in a solventborne coating composition and every, or substantially every, carboxyl group of the second intermediate product is reacted with a monoepoxide compound. In other embodiments, on average some of the carboxyl groups are left unreacted and may be neutralized, for example with ammonia, an amine, or another base in forming a waterborne coating composition.

Coating Compositions of the Wax-Modified Flexible Hyperbranched Polyol

A desired amount of the wax-modified flexible hyperbranched polyol is included in the coating composition. The amount of the wax-modified flexible hyperbranched polyol included is not particularly limited and may vary depending on the characteristics of other coating components and the desired overall balance of performance characteristics of the coating obtained from the coating composition. In various examples, the coating composition may include from about 1% to about 80%, or from about 2% to about 75%, or from about 3% to about 70%, or 4% to about 65% by weight, or from about 5% to about 50% by weight, or from about 5% to about 45% by weight, or from about 10% to about 50% by weight, or from about 10% to about 45% by weight, or from about 10% to about 40% by weight, or from about 10% to about 35% by weight, or from about 15% to about 40% by weight, or from about 15% to about 35% by weight of the wax-modified flexible hyperbranched polyol based on the total amount of film-forming materials (also called the binder or vehicle of the coating composition).

The coating composition may include other reactive resins or polymers. Examples of useful resins or polymers include (meth)acrylate polymers (also known as acrylic polymers or resins), polyesters, polyethers, polyurethanes, polyols based on natural oils, such as those available under the trademark Polycins from Vertellus Specialties Inc, Indianapolis, Ind., for example a polyol based on castor oil, polysiloxanes, and those described in Mormile et al., U.S. Pat. No. 5,578,675; Lane et al US Patent Application Publication No. 2011/0135832; and Groenewolt et al., U.S. Patent Application Publication No. 2013/0136865, each of which is incorporated herein by reference. The other resins or polymers may have functionality reactive with the crosslinker for the hyperbranched polyol, or that the coating composition may contain a further crosslinker for the other resins or polymer. In certain preferred examples, the coating composition includes a further resin or polymer having hydroxyl groups, carbamate groups, or a combination of such groups. In various embodiments, the coating composition contains a hydroxyl-functional acrylic polymer, hydroxyl-functional polyester, or hydroxyl-functional polyurethane.

Polyvinyl polyols, such as acrylic (polyacrylate) polyol polymers that may be used as the hydroxy-functional material. Acrylic polymers or polyacrylate polymers may be copolymers of both acrylic and methacrylic monomers as well as other copolymerizable vinyl monomers. The term "(meth)acrylate" is used for convenience to designate either or both acrylate, and methacrylate, and the term "(meth)acrylic" is used for convenience to designate either or both acrylic and methacrylic.

Hydroxyl-containing monomers include hydroxy alkyl esters of acrylic or methacrylic acid. Nonlimiting examples of hydroxyl-functional monomers include hydroxyethyl (meth)acrylate, hydroxypropyl(meth)acrylates, hydroxybutyl(meth)acrylates, hydroxyhexyl(meth)acrylates, propylene glycol mono(meth)acrylate, 2,3-dihydroxypropyl(meth) acrylate, pentaerythritol mono(meth)acrylate, polypropylene glycol mono(meth)acrylates, polyethylene glycol mono (meth)acrylates, reaction products of these with epsilon-caprolactone, and other hydroxyalkyl(meth)acrylates having branched or linear alkyl groups of up to about 10 carbons, and mixtures of these, where the term "(meth)acrylate" indicates either or both of the methacrylate and acrylate esters. Generally, at least about 5% by weight hydroxyl-functional monomer is included in the polymer. Hydroxyl groups on a vinyl polymer such as an acrylic polymer can be generated by other means, such as, for example, the ring opening of a glycidyl group, for example from copolymerized glycidyl methacrylate, by an organic acid or an amine.

Hydroxyl functionality may also be introduced through thio-alcohol compounds, including, without limitation, 3-mercapto-1-propanol, 3-mercapto-2-butanol, 11-mercapto-1-undecanol, 1-mercapto-2-propanol, 2-mercaptoethanol, 6-mercapto-1-hexanol, 2-mercaptobenzyl alcohol, 3-mercapto-1,2-proanediol, 4-mercapto-1-butanol, and combinations of these. Any of these methods may be used to prepare a useful hydroxyl-functional acrylic polymer.

Examples of suitable comonomers that may be used include, without limitation, α,β-ethylenically unsaturated monocarboxylic acids containing 3 to 5 carbon atoms such as acrylic, methacrylic, and crotonic acids and the alkyl and cycloalkyl esters, nitriles, and amides of acrylic acid, methacrylic acid, and crotonic acid; α,β-ethylenically unsaturated dicarboxylic acids containing 4 to 6 carbon atoms and the anhydrides, monoesters, and diesters of those acids; vinyl esters, vinyl ethers, vinyl ketones, and aromatic or heterocyclic aliphatic vinyl compounds. Representative examples of suitable esters of acrylic, methacrylic, and crotonic acids include, without limitation, those esters from reaction with saturated aliphatic alcohols containing 1 to 20 carbon atoms, such as methyl, ethyl, propyl, isopropyl, n-butyl, isobutyl, tert-butyl, hexyl, 2-ethylhexyl, dodecyl, 3,3,5-trimethylhexyl, stearyl, lauryl, cyclohexyl, alkyl-substituted cyclohexyl, alkanol-substituted cyclohexyl, such as 2-tert-butyl and 4-tert-butyl cyclohexyl, 4-cyclohexyl-1-butyl, 2-tert-butyl cyclohexyl, 4-tert-butyl cyclohexyl, 3,3,5, 5-tetramethyl cyclohexyl, tetrahydrofurfuryl, and isobornyl acrylates, methacrylates, and crotonates; unsaturated dialkanoic acids and anhydrides such as fumaric, maleic, itaconic acids and anhydrides and their mono- and diesters with alcohols such as methanol, ethanol, propanol, isopropanol, butanol, isobutanol, and tert-butanol, like maleic anhydride, maleic acid dimethyl ester and maleic acid monohexyl ester; vinyl acetate, vinyl propionate, vinyl ethyl ether, and vinyl ethyl ketone; styrene, a-methyl styrene, vinyl toluene, 2-vinyl pyrrolidone, and p-tert-butylstyrene.

The acrylic polymer may be prepared using conventional techniques, such as by heating the monomers in the presence of a polymerization initiating agent and optionally a chain transfer agent. The polymerization may be carried out in solution, for example. Typical initiators are organic peroxides such as dialkyl peroxides such as di-t-butyl peroxide, peroxyesters such as t-butyl peroxy 2-ethylhexanoate, and t-butyl peracetate, peroxydicarbonates, diacyl peroxides, hydroperoxides such as t-butyl hydroperoxide, and peroxyketals; azo compounds such as 2,2'azobis(2-methylbutanenitrile) and 1,1'-azobis(cyclohexanecarbonitrile); and combinations of these. Typical chain transfer agents are mercaptans such as octyl mercaptan, n- or tert-dodecyl mercaptan; halogenated compounds, thiosalicylic acid, mercaptoacetic acid, mercaptoethanol and the other thiol alcohols already mentioned, and dimeric alpha-methyl styrene.

The reaction is usually carried out at temperatures from about 20° C. to about 200° C. The reaction may conveniently be done at the temperature at which the solvent or solvent mixture refluxes, although with proper control a temperature below the reflux may be maintained. The initiator should be chosen to match the temperature at which the reaction is carried out, so that the half-life of the initiator at that temperature should preferably be no more than about thirty minutes. Further details of addition polymerization generally and of polymerization of mixtures including (meth) acrylate monomers is readily available in the polymer art. The solvent or solvent mixture is generally heated to the reaction temperature and the monomers and initiator(s) are added at a controlled rate over a period of time, usually between 2 and 6 hours. A chain transfer agent or additional solvent may be fed in also at a controlled rate during this time. The temperature of the mixture is then maintained for a period of time to complete the reaction. Optionally, additional initiator may be added to ensure complete conversion.

Oligomeric and polymeric ethers may be used, including diethylene glycol, triethylene glycol, tetraethylene glycol, pentaethylene glycol, dipropylene glycol, tripropylene glycol, linear and branched polyethylene glycols, polypropylene glycols, and block copolymers of poly(ethylene oxide-co-propylene oxide). Other polymeric polyols may be obtained by reacting a polyol initiator, e.g., a diol such as 1,3-propanediol or ethylene or propylene glycol or a polyol such as trimethylolpropane or pentaerythritol, with a lactone or alkylene oxide chain-extension reagent. Lactones that can be ring opened by active hydrogen are well known in the art. Examples of suitable lactones include, without limitation, epsilon.-caprolactone, gamma.-caprolactone, beta.-butyrolactone, beta.-propriolactone, gamma.-butyrolactone, alpha-methyl-gamma.-butyrolactone, beta-methyl-gamma.-butyrolactone, gamma.-valerolactone, .delta-valerolactone, gamma-decanolactone, delta-decanolactone, gamma-nonanoic lactone, gamma-octanoic lactone, and combinations of these. In one preferred embodiment, the lactone is epsilon-caprolactone. Useful catalysts include those mentioned above for polyester synthesis. Alternatively, the reaction can be initiated by forming a sodium salt of the hydroxyl group on the molecules that will react with the lactone ring. Similar polyester polyols may be obtained by reacting polyol initiator molecules with hydroxy acids, such as 12-hydroxystearic acid.

In other embodiments, a polyol initiator compound may be reacted with an oxirane-containing compound to produce a polyether diol to be used in the polyurethane elastomer polymerization. Alkylene oxide polymer segments include, without limitation, the polymerization products of ethylene oxide, propylene oxide, 1,2-cyclohexene oxide, 1-butene oxide, 2-butene oxide, 1-hexene oxide, tert-butylethylene oxide, phenyl glycidyl ether, 1-decene oxide, isobutylene oxide, cyclopentene oxide, 1-pentene oxide, and combinations of these. The oxirane-containing compound is preferably selected from ethylene oxide, propylene oxide, butylene oxide, tetrahydrofuran, and combinations of these. The alkylene oxide polymerization is typically base-catalyzed. The polymerization may be carried out, for example, by charging the hydroxyl-functional initiator compound and a catalytic amount of caustic, such as potassium hydroxide, sodium methoxide, or potassium tert-butoxide, and adding the alkylene oxide at a sufficient rate to keep the monomer available for reaction. Two or more different alkylene oxide monomers may be randomly copolymerized by coincidental addition or polymerized in blocks by sequential addition. Homopolymers or copolymers of ethylene oxide or propylene oxide are preferred. Tetrahydrofuran may be polymerized by a cationic ring-opening reaction using such counterions as $SbF_6^-$, $AsF_6^-$, $PF_6^-$, $SbCl_6^-$, $BF_4^-$, $CF_3SO_3^-$, $FSO_3$, and $ClO_4^-$. Initiation is by formation of a tertiary oxonium ion. The polytetrahydrofuran segment can be prepared as a "living polymer" and terminated by reaction with the hydroxyl group of a diol such as any of those mentioned above. Polytetrahydrofuran is also known as polytetramethylene ether glycol (PTMEG). Any of the polyols mentioned above maybe employed as the polyol initiator and extended in this fashion.

Nonlimiting examples of suitable polycarbonate polyols that might be used include those prepared by the reaction of polyols with dialkyl carbonates (such as diethyl carbonate), diphenyl carbonate, or dioxolanones (such as cyclic carbonates having five- and six-member rings) in the presence of catalysts like alkali metal, tin catalysts, or titanium compounds. Useful polyols include, without limitation, any of those already mentioned. Aromatic polycarbonates are usually prepared from reaction of bisphenols, e.g., bisphenol A, with phosgene or diphenyl carbonate. Aliphatic polycarbonates may be preferred for a higher resistance to yellowing, particularly when the carbamate-functional material is used in an automotive OEM or refinish topcoat.

Polyesters polyols may be prepared by reacting: (a) polycarboxylic acids or their esterifiable derivatives, together if desired with monocarboxylic acids, (b) polyols, together if desired with monofunctional alcohols, and (c) if desired, other modifying components. Nonlimiting examples of polycarboxylic acids and their esterifiable derivatives include phthalic acid, isophthalic acid, terephthalic acid, halophthalic acids such as tetrachloro- or tetrabromophthalic acid, adipic acid, glutaric acid, azelaic acid, sebacic acid, fumaric acid, maleic acid, trimellitic acid, pyromellitic acid, tetrahydrophthalic acid, hexahydrophthalic acid, 1,2-cyclohexanedicarboxlic acid, 1,3-cyclohexane-discarboxlic acid, 1,4-cyclohexane-dicarboxlic acid, 4-methylhexahydrophthalic acid, endomethylenetetrahydropthalic acid, tricyclodecanedicarboxlic acid, endoethylenehexahydropthalic acid, camphoric acid, cyclohexanetetracarboxlic acid, and cyclobutanetetracarboxylic acid. The cycloaliphatic polycarboxylic acids may be employed either in their cis or in their trans form or as a mixture of the two forms. Esterifiable derivatives of these polycarboxylic acids include their single or multiple esters with aliphatic alcohols having 1 to 4 carbon atoms or hydroxy alcohols having up to 4 carbon atoms, preferably the methyl and ethyl ester, as well as the anhydrides of these polycarboxylic acids, where they exist. Nonlimiting examples of suitable monocarboxylic acids that can be used together with the polycarboxylic acids include benzoic acid, tert-butylbenzoic acid, lauric acid, isononanoic acid and fatty acids of naturally occurring oils. Nonlimiting examples of suitable polyols include any of those already mentioned above, such as ethylene glycol, butylene glycol, neopentyl glycol, propanediols, butanediols, hexanediols, diethylene glycol, cyclohexanediol, cyclohexanedimethanol, trimethylpentanediol, ethylbutylpropanediol ditrimethylolpropane, trimethylolethane, trimethylolpropane, glycerol, pentaerythritol, dipentaerythritol, tris-hydroxyethyl isocyanate, polyethylene glycol, polypropylene glycol, and polyols derived from natural oils. Nonlimiting examples of monoalcohols that may be used together with the polyols include butanol, octanol, lauryl alcohol, and ethoxylated and propoxylated phenols. Nonlimiting examples of suitable modifying components include compounds which contain a group which is reactive with respect to the functional groups of the polyester, including polyisocyanates and/or diepoxide compounds, and also if desired, monoisocyanates and/or monoepoxide compounds. The polyester polymerization may be carried out by known standard methods. This reaction is conventionally carried out at temperatures of between 180° C. and 280° C., in the presence if desired of an appropriate esterification catalyst. Typical catalysts for the esterification polymerization are protonic acids, Lewis acids, titanium alkoxides, and dialkyltin oxides, for example lithium octanoate, dibutyltin oxide, dibutyltin dilaurate, para-toluenesulfonic acid under reflux with small quantities of a suitable solvent as entraining agent such as an aromatic hydrocarbon, for example xylene, or a (cyclo)aliphatic hydrocarbon, for example cyclohexane.

Polyurethanes having hydroxyl functional groups may also be used in the coating compositions along with the wax-modified flexible hyperbranched polyol. Examples of suitable polyurethane polyols include polyester-polyurethanes, polyether-polyurethanes, and polycarbonate-polyurethanes, including, without limitation, polyurethanes polymerized using as polymeric diol reactants polyethers and polyesters including polycaprolactone polyesters or polycarbonate diols. These polymeric diol-based polyurethanes are prepared by reaction of the polymeric diol (polyester diol, polyether diol, polycaprolactone diol, polytetrahydrofuran diol, or polycarbonate diol), one or more polyisocyanates, and, optionally, one or more chain extension compounds. Chain extension compounds, as the term is being used, are compounds having two or more functional groups, preferably two functional groups, reactive with isocyanate groups, such as the diols, amino alcohols, and diamines. Preferably the polymeric diol-based polyurethane is substantially linear (i.e., substantially all of the reactants are difunctional).

Diisocyanates used in making the polyurethane polyols may be aromatic, aliphatic, or cycloaliphatic. Useful diisocyanate compounds include, without limitation, isophorone diisocyanate (IPDI), methylene bis-4-cyclohexyl isocyanate ($H_{12}$MDI), cyclohexyl diisocyanate (CHDI), m-tetramethyl xylene diisocyanate (m-TMXDI), p-tetramethyl xylene diisocyanate (p-TMXDI), 4,4'-methylene diphenyl diisocyanate (MDI, also known as 4,4'-diphenylmethane diisocyanate), 2,4- or 2,6-toluene diisocyanate (TDI), ethylene diisocyanate, 1,2-diisocyanatopropane, 1,3-diisocyanatopropane, 1,6-diisocyanatohexane (hexamethylene diisocyanate or HDI), 1,4-butylene diisocyanate, lysine diisocyanate, meta-xylylenediioscyanate and para-xylylenediisocyanate, 4-chloro-1,3-phenylene diisocyanate, 1,5-tetrahydro-naphthalene diisocyanate, 4,4'-dibenzyl diisocyanate, and xylylene diisocyanate (XDI), and combinations of these. Nonlimiting examples of higher-functionality polyisocyanates that may be used in limited amounts to produce branched thermoplastic polyurethanes (optionally along with monofunctional alcohols or monofunctional isocyanates) include 1,2,4-benzene triisocyanate, 1,3,6-hexamethylene triisocyanate, 1,6,11-undecane triisocyanate, bicycloheptane triisocyanate, triphenylmethane-4,4',4"-triisocyanate, isocyanurates of diisocyanates, biurets of diisocyanates, allophanates of diisocyanates, and the like. These and other diisocyanates and other higher-functional isocyanates can also be used to make urethane cured coatings by reaction with hydroxyl groups of the wax-modified flexible hyperbranched polyol. At a minimum, the wax-modified flexible hyperbranched polyol has hydroxyl groups as a result of the reaction in step (c) where the epoxide group is reacted with a carboxylic acid function.

In various embodiments, the polymeric diol preferably has a weight average molecular weight of at least about 500, more preferably at least about 1000, and even more preferably at least about 1800 and a weight average molecular weight of up to about 10,000, but polymeric diols having weight average molecular weights of up to about 5000, especially up to about 4000, may also be preferred. The polymeric diol advantageously has a weight average molecular weight in the range from about 500 to about 10,000, preferably from about 1000 to about 5000, and more preferably from about 1500 to about 4000. The weight average molecular weights may be determined by ASTM D-4274.

The reaction of the polyisocyanate, polymeric diol, and diol or other chain extension agent is typically carried out at an elevated temperature in the presence of a suitable catalyst, for example tertiary amines, zinc salts, and manganese salts. The ratio of polymeric diol, such as polyester diol, to extender can be varied within a relatively wide range depending largely on the desired hardness or flexibility of the final polyurethane elastomer. For example, the equivalent proportion of polyester diol to extender may be within the range of 1:0 to 1:12 and, more preferably, from 1:1 to 1:8. Preferably, the diisocyanate(s) employed are proportioned such that the overall ratio of equivalents of isocyanate to equivalents of active hydrogen containing materials is within the range of 1:1 to 1:1.05, and more preferably, 1:1 to 1:1.02. The polymeric diol segments typically are from about 35% to about 65% by weight of the polyurethane polymer, and preferably from about 35% to about 50% by weight of the polyurethane polymer.

A polysiloxane polyol may be made by hydrosilylating a polysiloxane containing silicon hydrides with an alkenyl polyoxyalkylene alcohol containing two or three terminal primary hydroxyl groups, for example allylic polyoxyalkylene alcohols such as trimethylolpropane monoallyl ether and pentaerythritol monoallyl ether.

Any of the polyol resins and polymers described above may be derivatized to have carbamate groups according to known methods, for example by reaction of a hydroxyl-functional material with an alkyl carbamate, for example methyl carbamate or butyl carbamate, through what is referred to as "transcarbamation" or "transcarbamoylation." In other methods of forming carbamate-functional resins and polymers for use in the coating compositions, the resin and polymers may be polymerized using a carbamate-functional monomer.

The coating composition containing the wax-modified flexible hyperbranched polyol and optional further active hydrogen-functional resin or polymer may also include at least one crosslinker or curing agent reactive with hydroxyl groups, such as aminoplast crosslinkers having active methylol, methylalkoxy or butylalkoxy groups; polyisocyanate crosslinkers, which may have blocked or unblocked isocyanate groups; polyanhydrides; and polyepoxide functional crosslinkers or curing agents, which could be reactive with the hydroxyls as well as with any carboxylic acid groups of the wax-modified flexible hyperbranched polyols.

Aminoplasts, or amino resins, are described in *Encyclopedia of Polymer Science and Technology* vol. 1, p. 752-789 (1985), the disclosure of which is hereby incorporated by reference. An aminoplast is obtained by reaction of an activated nitrogen with a lower molecular weight aldehyde, optionally with further reaction with an alcohol (preferably a mono-alcohol with one to four carbon atoms such as methanol, isopropanol, n-butanol, isobutanol, etC) to form an ether group. Preferred examples of activated nitrogens are activated amines such as melamine, benzoguanamine, cyclohexylcarboguanamine, and acetoguanamine; ureas, including urea itself, thiourea, ethyleneurea, dihydroxyethyleneurea, and guanylurea; glycoluril; amides, such as dicyandiamide; and carbamate-functional compounds having at least one primary carbamate group or at least two secondary carbamate groups. The activated nitrogen is reacted with a lower molecular weight aldehyde. The aldehyde may be selected from formaldehyde, acetaldehyde, crotonaldehyde, benzaldehyde, or other aldehydes used in making aminoplast resins, although formaldehyde and acetaldehyde, especially formaldehyde, are preferred. The activated nitrogen groups are at least partially alkylolated with the aldehyde, and may be fully alkylolated; preferably the activated nitrogen groups are fully alkylolated. The reaction may be catalyzed by an acid, e.g. as taught in U.S. Pat. No. 3,082,180, which is incorporated herein by reference.

The optional alkylol groups formed by the reaction of the activated nitrogen with aldehyde may be partially or fully etherified with one or more monofunctional alcohols. Suitable examples of the monofunctional alcohols include, without limitation, methanol, ethanol, n-propanol, isopropanol, n-butanol, isobutanol, tert-butyl alcohol, benzyl alcohol, and so on. Monofunctional alcohols having one to four carbon atoms and mixtures of these are preferred. The etherification may be carried out, for example, the processes disclosed in U.S. Pat. Nos. 4,105,708 and 4,293,692 incorporate the disclosures of which incorporated herein by reference. The aminoplast may be at least partially etherified, and in various embodiments the aminoplast is fully etherified. For example, the aminoplast compounds may have a plurality of methylol and/or etherified methylol, butylol, or alkylol groups, which may be present in any combination and along with unsubstituted nitrogen hydrogens. Examples of suitable curing agent compounds include, without limitation, melamine formaldehyde resins, including monomeric or polymeric melamine resins and partially or fully alkylated melamine resins, and urea resins (e.g., methylol ureas such as urea formaldehyde resin, and alkoxy ureas such as butylated urea formaldehyde resin). One nonlimiting example of a fully etherified melamine-formaldehyde resin is hexamethoxymethyl melamine.

The alkylol groups are capable of self reaction to form oligomeric and polymeric aminoplast crosslinking agents. Useful materials are characterized by a degree of polymerization. For melamine formaldehyde resins, it is preferred to use resins having a number average molecular weight less than about 2000, more preferably less than 1500, and even more preferably less than 1000.

A coating composition including aminoplast crosslinking agents may further include a strong acid catalyst to enhance the cure reaction. Such catalysts are well known in the art and include, for example, para-toluenesulfonic acid, dinonylnaphthalene disulfonic acid, dodecylbenzenesulfonic acid, phenyl acid phosphate, monobutyl maleate, butyl phosphate, and hydroxy phosphate ester. Strong acid catalysts are often blocked, e.g. with an amine.

Particularly for refinish coatings, polyisocyanate crosslinkers are commonly used. Examples of suitable polyisocyanate crosslinkers include, without limitation, alkylene polyisocyanates such as hexamethylene diisocyanate, 4- and/or 2,4,4-trimethylhexamethylene diisocyanate, dodecamethylene diisocyanate, 1,4-diisocyanatocyclohexane, 1-isocyanato-3,3,5-trimethyl-5-isocyanatomethylcyclohexane (isophorone diisocyanate), 2,4'- and/or 4,4'-diisocyanatodicyclohexylmethane, 3-isocyanato-methyl-3,5,5-trimethyl cyclohexyl isocyanate, aromatic polyisocyanates such as 2,4'- and/or 4,4'-diisocyanatodiphenylmethane, 2,4- and/or 2,6-diisocyanatotoluene, naphthylene diisocyanate, and mixtures of these polyisocyanates. Generally, polyisocyanates having three or more isocyanate groups are used; these may be derivatives or adducts of diisocyanates. Useful polyisocyanates may be obtained by reaction of an excess amount of an isocyanate with water, a polyol (for example, ethylene glycol, propylene glycol, 1,3-butylene glycol, neopentyl glycol, 2,2,4-trimethyl-1,3-pentane diol, hexamethylene glycol, cyclohexane dimethanol, hydrogenated bisphenol A, trimethylolpropane, trimethylolethane, 1,2,6-hexanetriol, glycerine, sorbitol or pentaerythritol), or by the reaction of the isocyanate with itself to give an isocyanurate. Examples include biuret-group-containing polyisocyanates, such as those described, for example, in U.S. Pat. Nos. 3,124,605 and 3,201,372 or DE-OS 1,101,394; isocyanurate-group-containing polyisocyanates, such as those described, for example, in U.S. Pat. No. 3,001,973, DE-PS 1,022,789, 1,222,067 and 1,027,394 and in DE-OS 1,929, 034 and 2,004,048; urethane-group-containing polyisocyanates, such as those described, for example, in DE-OS 953,012, BE-PS 752,261 or U.S. Pat. Nos. 3,394,164 and 3,644,457; carbodiimide group-containing polyisocyanates, such as those described in DE-PS 1,092,007, U.S. Pat. No. 3,152,162. and DE-OS 2,504,400, 2,537,685 and 2,552,350; allophanate group-containing polyisocyanates, such as those described, for example, in GB-PS 994,890, BE-PS 761,626 and NL-05 7,102,524; and uretdione group-containing polyisocyanates, such as those described in EP-A 0,377,177, each reference being incorporated herein by reference.

Such isocyanate crosslinkers for refinish coating compositions are commonly stored separately and combined with the hydroxyl-functional film-forming components shortly before application. For example, a two-part or two-pack or two-component refinish coating composition may include in a crosslinking part, package, or component one of aliphatic biurets and isocyanurates, such as the isocyanurates of hexamethylenediisocyanate and isophorone diisocyanate.

Curing catalysts for the urethane reaction such as tin catalysts can be used in the coating composition. Typical examples are without limitation, tin and bismuth compounds including dibutyltin dilaurate, dibutyltin oxide, and bismuth octoate. When used, catalysts are typically present in amounts of about 0.05 to 2 percent by weight tin based on weight of total nonvolatile vehicle.

A dianhydride may also be used to crosslink the hyperbranched polyol. Nonlimiting examples of di-cyclic carboxylic anhydrides include pyranyl dianhydride, ethylenediaminetetraacetic dianhydride, cyclobutane-1,2,3,4-tetracarboxylic dianhydride, 3,3',4,4'-biphenyltetracarboxylic dianhydride, tetrahydrofurane-2,3,4,5-tetracarboxylic dianhydride, and cyclohexane-1,2,4,5-tetracarboxylic acid dianhydride.

Polyepoxide crosslinking agents include acrylic polymers having epoxide groups, for example copolymers of allyl glycidyl ether, glycidyl acrylate, or glycidyl methacrylate, as well as polyglycidyl esters and ethers of polyol and polycarboxylic acids.

The coating composition made with the wax-modified flexible hyperbranched polyol may further include solvents, pigments, fillers, or customary additives.

A solvent may optionally be utilized in the coating compositions. Although the coating composition may be formulated, for example, in the form of a powder, it is often desirable that the composition be in a substantially liquid state, which can be accomplished with the use of a solvent to either dissolve or disperse the wax-modified flexible hyperbranched polyol, crosslinker, and other film-forming material or materials. In general, depending on the solubility characteristics of the components, the solvent can be any organic solvent and/or water. In one preferred embodiment, the solvent is a polar organic solvent. For example, the solvent may be a polar aliphatic solvent or polar aromatic solvent. Among useful solvents are ketone, ester, acetate, aprotic amide, aprotic sulfoxide, and aprotic amine solvents. Examples of specific useful solvents include ketones, such as acetone, methyl ethyl ketone, methyl amyl ketone, methyl isobutyl ketone, esters such as ethyl acetate, butyl acetate, pentyl acetate, ethyl ethoxypropionate, ethylene glycol butyl ether acetate, propylene glycol monomethyl ether acetate, aliphatic and/or aromatic hydrocarbons such as toluene, xylene, solvent naphtha, and mineral spirits, ethers such as glycol ethers like propylene glycol monomethyl ether, alcohols such as ethanol, propanol, isopropanol, n-butanol, isobutanol, and tert-butanol, nitrogen-containing compounds such as N-methyl pyrrolidone and N-ethyl pyrrolidone, and combinations of these. In example embodiments, the liquid medium is water or a mixture of water with small amounts of organic water-soluble or water-miscible co-solvents. The solvent in the coating composition may be present in an amount of from about 0.01 weight percent to about 99 weight percent, or in an amount of from about 10 weight percent to about 60 weight percent, or in an amount of from about 30 weight percent to about 50 weight percent.

When the coating compositions are formulated as basecoat topcoats, monocoat topcoats, or primers they contain pigments and fillers, including special effect pigments. Nonlimiting examples of special effect pigments that may be utilized in basecoat and monocoat topcoat coating compositions include metallic, pearlescent, and color-variable effect flake pigments. Metallic (including pearlescent, and color-variable) topcoat colors are produced using one or more special flake pigments. Metallic colors are generally defined as colors having gonioapparent effects. For example, the American Society of Testing Methods (ASTM) document F284 defines metallic as "pertaining to the appearance of a gonioapparent material containing metal flake." Metallic basecoat colors may be produced using metallic flake pigments like aluminum flake pigments, coated aluminum flake pigments, copper flake pigments, zinc flake pigments, stainless steel flake pigments, and bronze flake pigments and/or using pearlescent flake pigments including treated micas like titanium dioxide-coated mica pigments and iron oxide-coated mica pigments to give the coatings a different appearance (degree of reflectance or color) when viewed at different angles. Metal flakes may be cornflake type, lenticular, or circulation-resistant; micas may be natural, synthetic, or aluminum oxide type. Flake pigments do not agglomerate and are not ground under high shear because high shear would break or bend the flakes or their crystalline morphology, diminishing or destroying the gonioapparent effects. The flake pigments are satisfactorily dispersed in a binder component by stiffing under low shear. The flake pigment or pigments may be included in the high solids coating composition in an amount of about 0.01 wt. % to about 50 wt. % or about 15 wt. % to about 25 wt. %, in each case based on total binder weight. Nonlimiting examples of commercial flake pigments include PALIOCROME® pigments, available from BASF Corporation.

Nonlimiting examples of other suitable pigments and fillers that may be utilized in basecoat and monocoat topcoat coating compositions include inorganic pigments such as titanium dioxide, barium sulfate, carbon black, ocher, sienna, umber, hematite, limonite, red iron oxide, transparent red iron oxide, black iron oxide, brown iron oxide, chromium oxide green, strontium chromate, zinc phosphate, silicas such as fumed silica, calcium carbonate, talc, barytes, ferric ammonium ferrocyanide (Prussian blue), and ultramarine, and organic pigments such as metallized and nonmetallized azo reds, quinacridone reds and violets, perylene reds, copper phthalocyanine blues and greens, carbazole violet, monoarylide and diarylide yellows, benzimidazolone yellows, tolyl orange, naphthol orange, nanoparticles based on silicon dioxide, aluminum oxide or zirconium oxide, and so on. The pigment or pigments are preferably dispersed in a resin or polymer or with a pigment dispersant, such as binder resins of the kind already described, according to known methods. In general, the pigment and dispersing resin, polymer, or dispersant are brought into contact under a shear high enough to break the pigment agglomerates down to the primary pigment particles and to wet the surface of the pigment particles with the dispersing resin, polymer, or dispersant. The breaking of the agglomerates and wetting of the primary pigment particles are important for pigment stability and color development. Pigments and fillers may be utilized in amounts typically of up to about 60% by weight, based on total weight of the coating composition. The amount of pigment used depends on the nature of the pigment and on the depth of the color and/or the intensity of the effect it is intended to produce, and also by the dispersibility of the pigments in the pigmented coating composition. The pigment content, based in each case on the total weight of the pigmented coating composition, is preferably 0.5% to 50%, more preferably 1% to 30%, very preferably 2% to 20%, and more particularly 2.5% to 10% by weight.

Clearcoat coating compositions typically include no pigment, but may include small amount of colorants or fillers that do not unduly affect the transparency or desired clarity of the clearcoat coating layer produced from the composition.

Additional desired, customary coating additives agents may be included, for example, surfactants, stabilizers, wetting agents, dispersing agents, adhesion promoters, UV absorbers, hindered amine light stabilizers such as HALS compounds, benzotriazoles or oxalanilides; free-radical scavengers; slip additives; defoamers; reactive diluents, of the kind which are common knowledge from the prior art; wetting agents such as siloxanes, fluorine compounds, carboxylic monoesters, phosphoric esters, polyacrylic acids and their copolymers, for example polybutyl acrylate, or polyurethanes; adhesion promoters such as tricyclodecanedimethanol; flow control agents; film-forming assistants such as cellulose derivatives; rheology control additives, such as the additives known from patents WO 94/22968, EP-A-0 276 501, EP-A-0 249 201 or WO 97/12945; crosslinked polymeric microparticles, as disclosed for example in EP-A-0 008 127; inorganic phyllosilicates such as aluminum-magnesium silicates, sodium-magnesium and sodium-magnesium-fluorine-lithium phyllosilicates of the montmorillonite type; silicas such as Aerosils®; or synthetic polymers containing ionic and/or associative groups such as polyvinyl alcohol, poly(meth)acrylamide, poly(meth)acrylic acid, polyvinylpyrrolidone, styrene-maleic anhydride copolymers or ethylene-maleic anhydride copolymers and their derivatives, or hydrophobically modified ethoxylated urethanes or polyacrylates; flame retardant; and so on. Typical coating compositions include one or a combination of such additives.

Coating compositions can be coated by any of a number of techniques well known in the art. These include, for example, spray coating, dip coating, roll coating, curtain coating, knife coating, spreading, pouring, dipping, impregnating, trickling or rolling, and the like. For automotive body panels, spray coating is typically used. Preference is given to employing spray application methods, such as compressed-air spraying, airless spraying, high-speed rotation, electrostatic spray application, alone or in conjunction with hot spray application such as hot-air spraying, for example.

The coating compositions and coating systems described herein are employed in particular in the technologically and esthetically particularly demanding field of automotive OEM finishing and also of automotive refinish. The coating compositions can be used in both single-stage and multistage coating methods, particularly in methods where a pigmented basecoat or monocoat coating layer is first applied to an uncoated or precoated substrate and afterward another coating layer may optionally be applied when the pigmented film is a basecoat coating. The invention, accordingly, also provides multicoat coating systems comprising at least one pigmented basecoat and may have least one clearcoat disposed thereon, wherein either the clearcoat or the basecoat has been or both have been produced from the coating composition containing the wax-modified flexible hyperbranched polyol as disclosed herein. Both the basecoat and the clearcoat coating composition can include the disclosed wax-modified flexible hyperbranched polyol.

The applied coating compositions can be cured after a certain rest time or "flash" period. The rest time serves, for example, for the leveling and devolatilization of the coating films or for the evaporation of volatile constituents such as solvents. The rest time may be assisted or shortened by the application of elevated temperatures or by a reduced humidity, provided this does not entail any damage or alteration to the coating films, such as premature complete crosslinking, for instance. The thermal curing of the coating compositions has no peculiarities in terms of method but instead takes place in accordance with the typical, known methods such as heating in a forced-air oven or irradiation with IR lamps. The thermal cure may also take place in stages. Another preferred curing method is that of curing with near infrared (NIR) radiation. Although various methods of curing may be used, heat curing is preferred. Generally, heat curing is effected by exposing the coated article to elevated temperatures provided primarily by radiative heat sources. After application, the applied coating layer is cured, for example with heat at temperatures from 30 to 200° C., or from 40 to 190° C., or from 50 to 180° C., for a time of 1 min up to 10 h, more preferably 2 min up to 5 h, and in particular 3 min to 3 h, although longer cure times may also be employed at the temperatures employed for automotive refinish, which are preferably between 30 and 90° C. The wax-modified flexible hyperbranched polyol can be used for both refinish coatings and for original finish coatings that are cured at higher temperatures. A typical method for applying a refinish coating composition includes application and drying with cure at room temperature or at an elevated temperature between 30 and 90° C. OEM coatings are typically cured at higher temperatures, for example from about 110 to about 135° C. The curing time will vary depending on the particular components used, and physical parameters such as the thickness of the layers, however, typical curing times range from about 15 to about 60 minutes, and preferably about 15-25 minutes for blocked acid catalyzed systems and about 10-20 minutes for unblocked acid catalyzed systems.

Cured basecoat layers formed may have a thickness of from about 5 to about 75 .mu.m, depending mainly upon the color desired and the thickness needed to form a continuous layer that will provide the color. Cured clearcoat layers formed typically have thicknesses of from about 30 μm to about 65 μm.

The coating composition can be applied onto many different types of substrates, including metal substrates such as bare steel, phosphated steel, galvanized steel, or aluminum; and non-metallic substrates, such as plastics and composites. The substrate may also be any of these materials having upon it already a layer of another coating, such as a layer of an electrodeposited primer, primer surfacer, and/or basecoat, cured or uncured.

The substrate may be first primed with an electrodeposition (electrocoat) primer. The electrodeposition composition can be any electrodeposition composition used in automotive vehicle coating operations. Non-limiting examples of electrocoat compositions include electrocoating compositions sold by BASF. Electrodeposition coating baths usually comprise an aqueous dispersion or emulsion including a principal film-forming epoxy resin having ionic stabilization (e.g., salted amine groups) in water or a mixture of water and organic cosolvent. Emulsified with the principal film-forming resin is a crosslinking agent that can react with functional groups on the principal resin under appropriate conditions, such as with the application of heat, and so cure the coating. Suitable examples of crosslinking agents, include, without limitation, blocked polyisocyanates. The electrodeposition coating compositions usually include one or more pigments, catalysts, plasticizers, coalescing aids, antifoaming aids, flow control agents, wetting agents, surfactants, UV absorbers, HALS compounds, antioxidants, and other additives.

The electrodeposition coating composition is preferably applied to a dry film thickness of 10 to 35 μm. After application, the coated vehicle body is removed from the bath and rinsed with deionized water. The coating may be cured under appropriate conditions, for example by baking at from about 135° C. to about 190° C. for between about 15 and about 60 minutes.

Because the coatings of the invention produced from the coating compositions of the invention adhere excellently even to electrocoats, surfacer coats, basecoat systems or typical, known clearcoat systems that have already cured, they are outstandingly suitable not only for use in automotive OEM finishing but also for automotive refinish or for the modular scratchproofing of automobile bodies that have already been painted.

A coating produced from the coating composition containing the wax-modified flexible hyperbranched polyol has excellent durability, low volatile organic content, and improved flexibility, particularly at low temperatures.

Wax-Modified Hyperbranched Polyols

The wax-modified hyperbranched polyol described hereinbelow is a wax-modified hyperbranched polyester polyol macromolecule having a plurality of both embedded and exterior hydroxyl groups with a branched hydrocarbon chain for flexibility thereon. In an embodiment a wax-modified hyperbranched polyol includes:

a) a central nucleus comprising a hydrocarbon structure with a plurality of oxygen atoms;

b) a first long-chain wax-like modifier and a first chain extension, both attached to the central nucleus, the first long-chain wax-like modifier being formed from a long-chain wax-like reactant comprising a carboxylic acid functionality, the first chain extension being formed from a compound comprising a carboxyl group and a plurality of hydroxyl groups;

c) an intermediate substituent attached to the first chain extension, the intermediate substituent being formed from a compound selected from the group consisting of polyfunctional carboxylic anhydrides and acids thereof, and d) a second chain extension attached to the intermediate substituent, the second chain extension comprising a hydroxyl group and being formed from a flexible hydrocarbon compound having a terminal or non-terminal epoxide group thereon.

Optionally, before the hydroxyl-functional first intermediate product prepared in step (a) is reacted with a cyclic carboxylic acid anhydride to form a carboxylic acid-functional second intermediate, the hydroxyl-functional first intermediate can be variably extended through the ring-opening reaction of the intermediate's hydroxyls with a lactone. The number of mols of lactone relative to the mols of the first intermediate will determine the degree of extension away from the core. See (a″) and (b) above. Non-limiting examples of suitable lactones include ε-Caprolactone, γ-Caprolactone, β-Butyrolactone, β-Propriolactone, γ-Butyrolactone, α-Methyl-γ-butyrolactone, β-Methyl-γ-butyrolactone, γ-Valerolactone, δ-Valerolactone, γ-Decanolactone, δ-Decanolactone, γ-Nonanoic lactone, γ-Octanoic lactone.

Another embodiment is a method of making a wax-modified hyperbranched polyester polyol. The method generally includes the steps of:

(a) reacting a polyol, preferably one comprising at least three hydroxyl groups, with (a') a long-chain wax-like reactant comprising a carboxylic acid functionality and (a″) a first chain extender, which contains a plurality of hydroxyl groups and also contains a carboxyl group, to form a first generation branched core;

(b) optionally, further reacting the first generation branched core with the first chain extender, to form a subsequent generation branched core;

(c) reacting the first or subsequent generation branched core with a compound selected from the group consisting of carboxylic anhydrides and acids to form an ester bridge therewith, thereby forming an intermediate polyester macromolecule; and (d) reacting the intermediate polyester macromolecule with a second chain extender having a terminal or non-terminal epoxide group and a branched hydrocarbon chain, to form a wax-modified hyperbranched polyol having both primary and secondary hydroxyl groups thereon.

Wax-modified hyperbranched polyols described herein, including those which are products of the above method, preferably exhibit the low viscosity needed for coatings operations. A preferred embodiment is a wax-modified hyperbranched polyester polyol having both exterior (primary) and partially embedded (secondary) hydroxyl groups in the structure thereof.

When referring to wax-modified hyperbranched polyols, the term "primary hydroxyl group" is intended to mean a hydroxyl group located at or near the outer periphery of the hyperbranched molecule, so as to be relatively accessible for reaction, and the term "secondary hydroxyl group" is intended to mean a hydroxyl group which is located deeper in the branched structure than the outer periphery, that is, which is at least partially embedded in the macromolecule.

As described above one method for preparing wax-modified hyperbranched polyols includes a first step of reacting a starter polyol with a long-chain wax-like reactant comprising a carboxylic acid functionality and with a first chain extender which contains a plurality of hydroxyl groups and also contains a carboxyl group, to form a first generation branched core.

In this first step, preferred starter polyols include all of those described above for the wax-modified flexible hyperbranched polyols, and have three or more reactive hydroxyl groups thereon. Triols such as glycerol, trimethylol propane, trimethylol butane and related structures are favored, although compounds having four hydroxyl groups thereon, such as pentaerythritol, five hydroxyl groups, six hydroxyl groups, etc. thereon may also be used as starter polyols. Preferably the starter polyol has 8 or less, preferably 6 or less, hydroxyl groups thereon. Mono- and di-saccharides are included such as sucrose, glucose, fructose, etc. A particularly preferred starter polyol, for use in forming the central core, is trimethylol propane (TMP).

Also in the first step, materials usable as the long-chain wax-like reactant comprising a carboxylic acid include all of those described above for the wax-modified flexible hyperbranched polyols such as linear and branched, unsubstituted C8-C85, preferably C12-C75, more preferably C14-C60 primary, secondary and tertiary carboxylic acids. Preferred carboxylic acids are unsubstituted linear saturated carboxylic acids. Preferred examples of long chain wax-like reactants useful herein include the UNICID™ acids available from Baker Hughes, which are long chain, linear primary carboxylic acids with carbon chain lengths from 25 to 50 carbons.

Also in the first step, materials usable as the first chain extender include carboxylic acids having two or more hydroxyl groups thereon, as well as carboxylic acids of the type described in which one or more of the hydroxyl groups have been hydroxyalkyl substituted. A particularly preferred material for use as the first chain extender is dimethylol propionic acid (DMPA), Gluconic acid and Lactobionic acid.

A conventional esterification catalyst may be used in this first step, if desired, such as sulfuric acid, dibutyltin oxide or other known catalyst. The reaction can occur stepwise, meaning that one or the other of the long-chain wax-like reactant comprising a carboxylic acid and the first chain extender is first reacted with the polyol to form a first stage intermediate followed by reaction of the other of the long-chain wax-like reactant comprising a carboxylic acid and the first chain extender with the first stage intermediate, or the reaction can take place essentially in one step where both the long-chain wax-like reactant comprising a carboxylic acid and the first chain extender are reacted with the polyol.

Optionally, this first generation branched core may be further reacted with the first chain extender, or with another different monomer having a similar structure as described above in connection with the first chain extender, one or more additional times, as desired, to cause further branching and growth thereof. Such additional polymerization of the first generation branched core, where used, forms a second, third, fourth, or higher generation branched core, as desired, and according to the particular needs under consideration.

The next step in the method of forming the wax-modified hyperbranched polyol involves reacting the branched core, at whatever level of generational branching is used, with an intermediate substituent which includes a polyfunctional carboxylic anhydride or acid thereof, to form an intermediate polyester macromolecule having reactive carboxyl groups thereon. The intermediate substituent may be the same as the cyclic carboxylic acid anhydride described above for the wax-modified flexible hyperbranched polyol, and may for example be selected from, e.g., phthalic acid, isophthalic acid, orthophthalic anhydride, tetrahydrophthalic anhydride, hexahydrophthalic anhydride, trimellitic anhydride, succinic anhydride and similar such compounds. Preferred materials for use as the intermediate compound are cyclic polyfunctional carboxylic anhydrides. Particularly preferred materials, for use as the intermediate substituent, are hexahydrophthalic anhydride (HHPA) and methyl, hexahydrophthalic anhydride.

The next step involves reacting the intermediate polyester macromolecule with a second chain extender to form a hyperbranched polyol macromolecule having both primary and secondary hydroxyl groups thereon.

The second chain extender is a flexible hydrocarbon compound having a terminal or non-terminal epoxide group thereon. The second chain extender may be the same as the epoxide-functional compound described above for the wax-modified flexible hyperbranched polyol, and may for example be selected from, e.g., the group consisting of glycidyl esters, glycidyl ethers, epoxides, epoxy resins, epoxidized acids, and epoxidized alcohols. Preferably, the second chain extender is selected from the group consisting of glycidyl esters and glycidyl ethers.

Some examples of possible compounds usable as the second chain extender include cyclohexane oxide, any aliphatic chain with terminal or non-terminal epoxide group such as, for example, cis 2,3-epoxybutane, 1-2-epoxybutane, 1-2-epoxyhexane, 1-2-epoxyoctane, 1-2-epoxydecane, cis-7,8-epoxy-2-methyloctadecane, hexafluoropropylene oxide, glycidyl neodecanoate, glycidyl neononanoate, and the glycidyl esters sold by the Shell Chemical/Momentive company under the trademark "Cardura". The above list is intended to be illustrative rather than limitative. Those skilled in the art will realize that many other compounds may be used.

In preparing the wax-modified hyperbranched polyol conditions, ratios, etc. used can be those described above for the wax-modified flexible hyperbranched polyol.

Coating Compositions Incorporating the Wax-Modified Hyperbranched Polyols

Compositions containing the wax-modified hyperbranched polyol can be prepared in the same way, can be used in the same way, can be formulated in the same way, etc. as described above for the wax-modified flexible hyperbranched polyol. For example, in formulating these coating compositions, the wax-modified hyperbranched polyols may be reacted with an aminoplast curing agent, or may be reacted with an isocyanate or isocyanurate, or may be reacted with combinations of aminoplasts and isocyanates and/or isocyanurates. Also, if some of the carboxylic acids are incorporated into the structure of the macromolecule and are left free, they can be used to cross-link with polyepoxides to form a flexible coating.

The cross-linkers can be drawn from a list of known melamine-formaldehyde resins, isocyanates and isocyanurates and polyepoxides. The list would include, and is not restricted to, compounds like Cymel-303, fully methylated hexamethoxymethylmelamine, partially methylated methoxymethylmelamine, butoxymethylmelamines, butoxy, methoxymethylmelamines, hexamethylenediisocyanate (HDI), isophoronediisocyanate(IPDI), cyclohexanediisocyanate(CHDI), toluenediisocyanate(TDI), methylenediphenylenediisocyanate (MDI), the isocyanurates derived from HDI, IPDI, CHDI, TDI, MDI, epoxides from the EPON series sold by the Shell Chemical company, bisphenol A type epoxides, acrylic polymers with glycidylacrylate or methacrylate as one of the monomers. Other ingredients that go into making the paint are well known to those knowledgeable in the art and would include flow additives for rheology control and leveling, solvents, catalysts.

When the curing takes place by reacting the hydroxyl groups of the wax-modified hyperbranched polyols, either melamine-formaldehyde resins or isocyanates/isocyanurates can be used by themselves or combinations of them may be used. Likewise, the carboxylic acids can be cured with polyepoxides either by themselves or can have additional curing perpetuated by melamine-formaldehyde or isocyanates/isocyanurates. The ratios of cross-linkers to the reacting groups can be between 2-0.1, preferably between 1.2-0.8, based on their equivalent weights. When both primary and secondary hydroxyls are present, the amounts of cross-linkers can be varied such that all the primary hydroxyls will react leaving the secondary hydroxyls free for adhesion purposes, or a fraction of these also reacted to give better humidity resistance.

In general, it has been found that with a dual cure (hydroxyls with melamine-formaldehyde and isocyanates or isocyanaurates, or carboxylic acids with epoxides and hydroxyls with melamine-formaldehyde or isocyanates or isocyanaurates), the resulting film exhibited excellent etch characteristics.

Preferred compounds according to the invention include those of the following formulae I, and II:

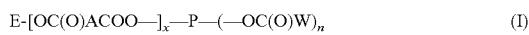
$$\text{E-[OC(O)ACOO—]}_x\text{—P—(—OC(O)W)}_n \qquad (I)$$

where:
P is a $C_3$-$C_{60}$ polyol moiety, bonded to x [OC(O)ACOO—] and n-(—OC(O)W) moieties through x+n —OH functionalities;
n is 1-2;
W is a $C_8$-$C_{60}$ linear or branched alkane moiety;
x is 0-8; preferably 1-8;
A is a $C_2$-$C_{22}$ substituted or unsubstituted aliphatic, alicyclic or aromatic moiety; and E is hydrogen or R—C(OH), where R is a substituted or unsubstituted $C_1$-$C_{22}$ aliphatic, alicyclic or aromatic moiety.

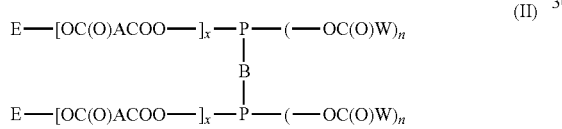

(II)

where:
P is a $C_3$-$C_{60}$ polyol moiety, bonded to x [OC(O)ACOO—] and n-(—OC(O)W) moieties through x+n —OH functionalities;
n is 1-2;
W is a $C_8$-$C_{60}$ linear or branched alkane moiety;
x is 0-8; preferably 1-8;
A is a $C_2$-$C_{22}$ substituted or unsubstituted aliphatic, alicyclic or aromatic moiety;
E is hydrogen or R—C(OH), where R is a substituted or unsubstituted $C_1$-$C_{22}$ aliphatic, alicyclic or aromatic moiety; and B is a substituted or unsubstituted $C_4$-$C_{36}$ aliphatic, alicyclic or aromatic moiety esterified to P through a P —OH functionality.

Other definitions of P, n, W, B, etc. in Formulae (I) and (II) above can be found in the above description of exemplary starting materials that can be used to prepare various polyols.

Other preferred compounds include those of the formulae (III) and (IV):

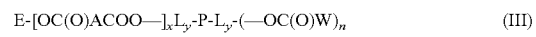
$$\text{E-[OC(O)ACOO—]}_x\text{L}_{y'}\text{-P-L}_{y'}\text{-(—OC(O)W)}_n \qquad (III)$$

where P, x, n, W, A and E are as described above for formula (I); and
where L is a (poly)lactone chain moiety where y is 1-5.

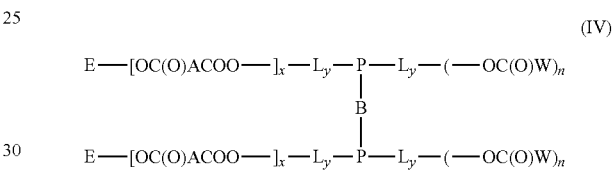

(IV)

where P, x, n, W, A, E, and B are as described above for formula (II); and
where L is a (poly)lactone chain moiety where y is 1-5.

Other definitions of P, n, W, B, L, y etc. in Formulae (III) and (IV) above can be found in the above description of exemplary starting materials that can be used to prepare various polyols.

Particularly preferred compounds are depicted below:

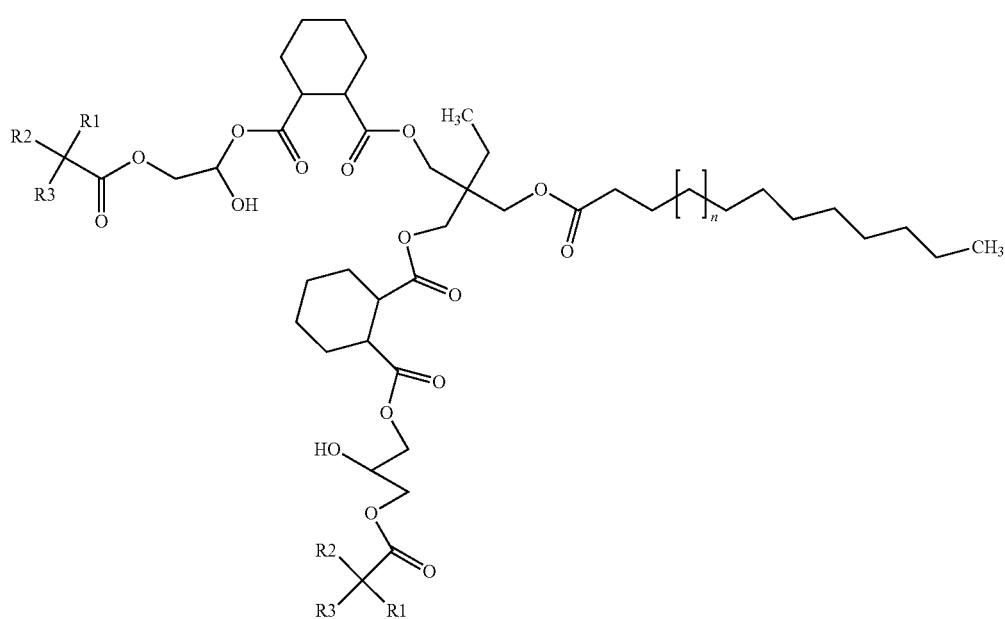

(V)

where n=14-39 and —OC(O)R1R2R3 is a branched C10 monocarboxylic acid residue.

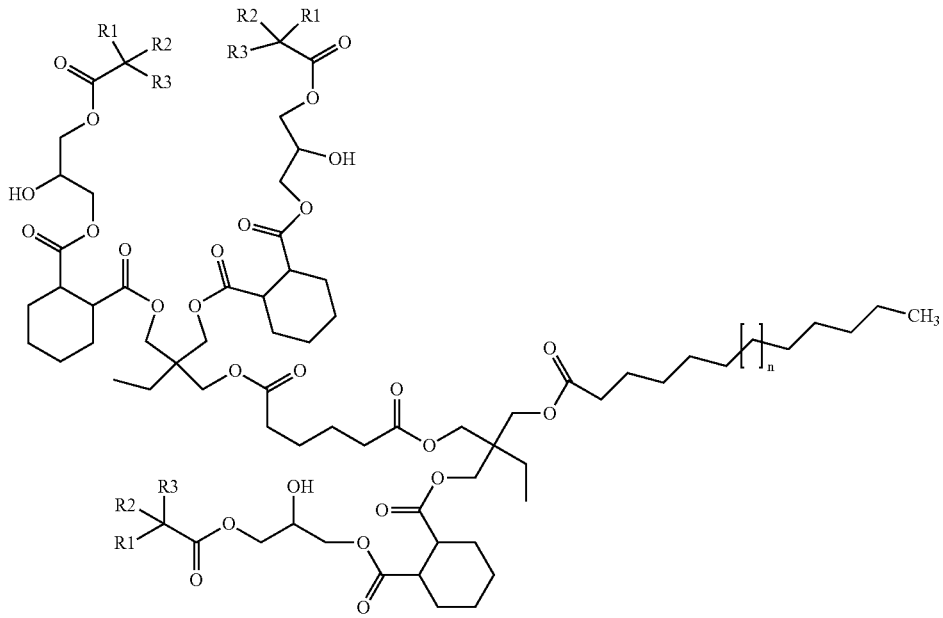

where n=14-39 and —OC(O)R1R2R3 is a branched C10 monocarboxylic acid residue.

EXAMPLES

Example 1. Synthesis of a Wax-Modified Hyperbranched Polyol

A reactor was charged with 4.891 parts by weight Trimethylolpropane, 10.231 parts by weight Unicid 700™, (by Baker Hughes), and 4.166 parts by weight mixed Xylenes. The contents of the reactor were mixed and heated to 170° C. and maintained there for about 8 hours. By-product water was removed as it was generated. The reaction product was cooled to about 100° C. and reduced with 2.008 parts by weight Aromatic 100 solvent. To the reactor was then added 7.024 parts by weight of molten Hexahydrophthalic anhydride (60° C.) and a flush of 0.733 parts by weight Aromatic 100. The contents of the reactor were stirred and heated to 115° C. After the exotherm peaked (keeping the temperature below 150° C.), the contents of the reactor were heated to 136° C., then cooled again to about 105° C. Then, an additional 7.024 parts by weight of molten Hexahydrophthalic anhydride (60° C.) were added followed by a flush of 0.733 parts by weight Aromatic 100. The contents of the reactor were stirred and heated to 120° C. After the exotherm peaked (keeping the temperature below 150° C.), the contents of the reactor were heated to 145° C. The temperature was maintained at 145° C. for 90 minutes, then cooled to about 142° C. Keeping the temperature between 140-148° C., 22.095 parts by weight of Cardura™E10-P, (glycidyl ester of Versatic™ acid obtained from Momentive, Columbus, Ohio), was added over about 90 minutes, followed by a flush of 0.820 parts by weight Aromatic 100. The reaction mixture was held at 145° C. for 3 hours, then cooled slowly to 106° C. and reduced with 3.827 parts by weight of mixed Xylenes. At 106° C., 36.448 parts by weight Oxsol 100 solvent was rapidly added and mixed into the reaction mixture. Heat was applied to prevent the batch temperature from dropping below 85° C. during the Oxsol 100 addition. Once the Oxsol 100 addition is completed, the batch is allowed to slowly cool for filtration and fill-off.

Example 2. Synthesis of a Wax-Modified, Flexible Hyperbranched Polyol

A reactor was charged with 5.961 parts by weight Trimethylolpropane, 7.780 parts by weight Unicid 700™, (by Baker Hughes), 3.124 parts by weight Adipic acid, 0.036 parts by weight Dibutyltin oxide, and 8.977 parts by weight mixed Xylenes. The contents of the reactor were mixed and heated to 195° C. and maintained there for about 6 hours until an acid value of about zero was achieved. By-product water was removed as it was Generated. The reaction product was cooled to about 100° C. and reduced with 5.877 parts by weight Aromatic 100 solvent. To the reactor was then added 12.352 parts by weight of molten Hexahydrophthalic anhydride (60° C.) and a flush of 1.197 parts by weight Aromatic 100 and 1.197 parts by weight mixed Xylenes. The contents of the reactor were stirred and heated to 115° C. After the exotherm peaked (keeping the temperature below 150° C.), the contents of the reactor were heated to 145° C. The temperature was maintained at 145° C. for 90 minutes, then cooled to about 142° C. Keeping the temperature between 140-148° C., 18.695 parts by weight of Cardura™E10-P, (glycidyl ester of Versatic™ acid obtained from Momentive, Columbus, Ohio), was added over about 30 minutes, followed by a flush of 0.754 parts by weight mixed Xylenes. The reaction mixture was held at 145° C. for 3 hours, then cooled slowly to about 109°. At 109° C., 34.063 parts by weight Oxsol 100 solvent was rapidly added and mixed into the reaction mixture. Heat was applied to prevent the batch temperature from dropping below 85° C. during the Oxsol 100 addition. Once the Oxsol 100 addition is completed, the batch is allowed to slowly cool for filtration and fill-off.

As used herein, the phrase "a compound that may be obtained by reaction . . . " and the like is not limited by the noted reaction and refers to a chemical product capable of being obtained by the noted reaction but not necessarily being so obtained. As is generally known in the art, there typically exists more than one synthetic pathway to a given compound, such pathways being readily envisioned by those of ordinary skill in the art given the noted reaction and/or structure of the compound and/or its reactants. In all events the compounds described herein, whether described by chemical formula or by a reaction scheme, are fully described and enabled chemical compounds, and need not be associated with a method for making.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out. For example, $C_2$-$C_{22}$ includes $C_2$ and $C_{22}$ as well as, e.g., $C_3$, $C_{12}$, $C_{17}$, etc.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The following claims are fully described and enabled by the above description, and are incorporated therein as a part thereof.

The invention claimed is:

1. A coating composition comprising a wax-modified flexible hyperbranched polyol, wherein the wax-modified flexible hyperbranched polyol is prepared by a process comprising:
    (a) reacting a polyol comprising at least three hydroxyl groups with (a') a $C_8$-$C_{85}$ linear or branched unsubstituted carboxylic acid and optionally with (a'') an aliphatic dicarboxylic acid having from 6 to 36 carbon atoms or an esterifiable derivative thereof, to form a hydroxyl-functional first intermediate product;
    (b) reacting the hydroxyl-functional first intermediate product with a cyclic carboxylic acid anhydride to form a carboxylic acid-functional second intermediate product; and
    (c) reacting the second intermediate product with an epoxide-functional compound having one epoxide group to form the wax modified flexible hyperbranched polyol.

2. The coating composition according to claim 1, wherein the wax-modified flexible hyperbranched polyol is prepared by a process comprising:
    (a) reacting a polyol comprising at least three hydroxyl groups with (a') a $C_8$-$C_{85}$ linear or branched unsubstituted carboxylic acid and with (a'') an aliphatic dicarboxylic acid having from 6 to 36 carbon atoms or an esterifiable derivative thereof, to form a hydroxyl-functional first intermediate product.

3. The coating composition according to claim 1, comprising 5% to 60% by weight of the wax-modified flexible hyperbranched polyol based on a total amount of film-forming materials in the coating composition, and comprising no silica.

4. The coating composition according to claim 3, further comprising at least one of a hydrogen-functional resin and hydrogen-functional polymer.

5. The coating composition according to claim 1, wherein the wax-modified flexible hyperbranched polyol has the following structure:

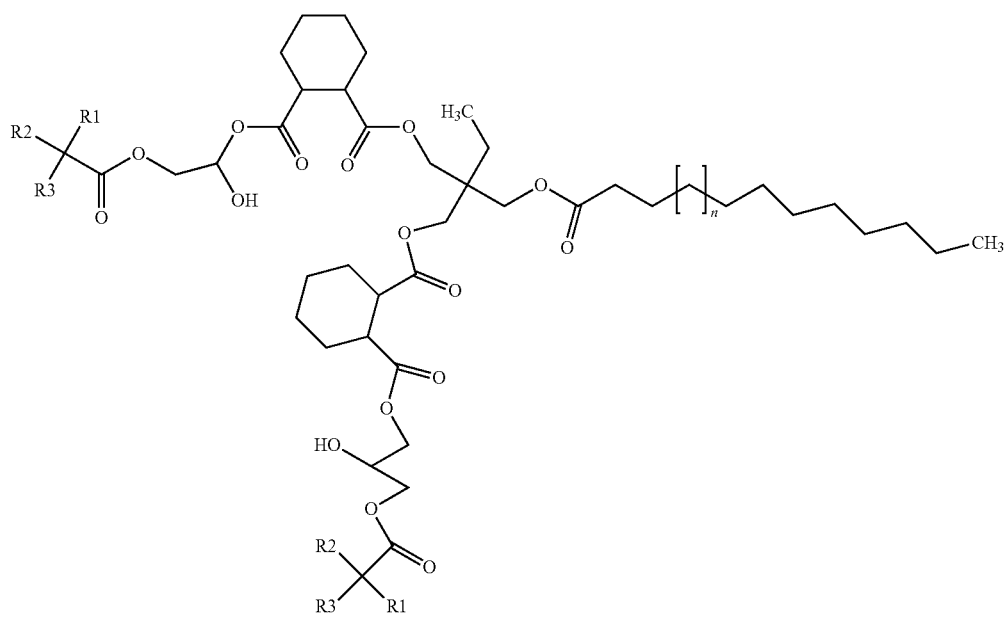

(V)

where n=14-39 and —OC(O)R1R2R3 is a branched C10 monocarboxylic acid residue.

6. The coating composition according to claim 1, wherein the wax-modified flexible hyperbranched polyol has the following structure:

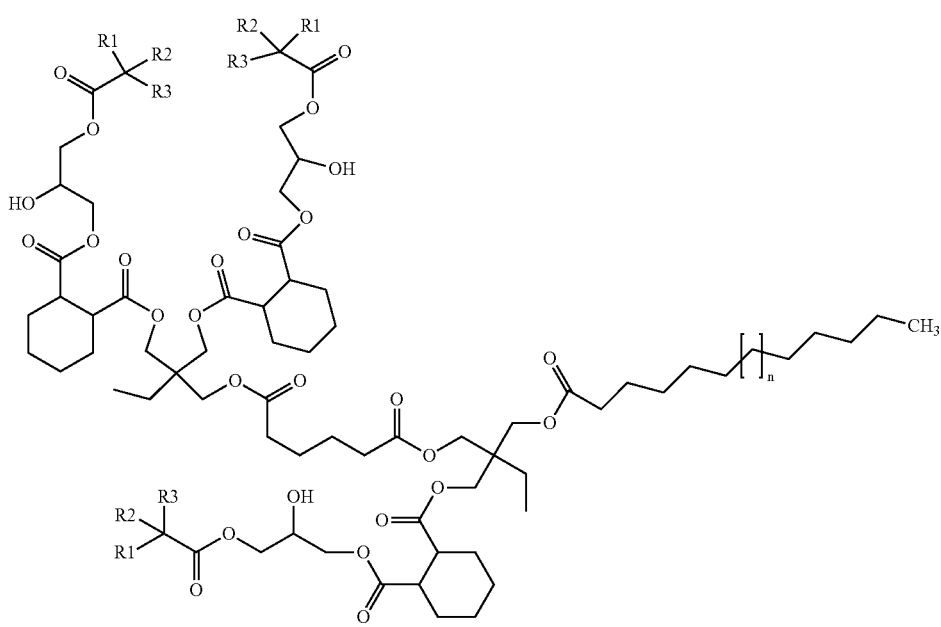

(VI)

where n=14-39 and —OC(O)R1R2R3 is a branched C10 monocarboxylic acid residue.

7. A method for coating a substrate, comprising applying to the substrate the coating composition of claim 1 to form a coating layer, and curing the coating layer.

8. A coating composition comprising a wax-modified hyperbranched polyol, wherein the wax-modified hyperbranched polyol is prepared by a process comprising:
  (a) reacting a polyol comprising at least three hydroxyl groups with (a') a $C_8$-$C_{85}$ linear or branched unsubstituted carboxylic acid and with (a") a first chain extender which comprises a plurality of hydroxyl groups and a carboxyl group, to form a first generation branched core;
  (b) optionally further reacting the first generation branched core with the first chain extender to form a subsequent generation branched core;
  (c) reacting the first or subsequent generation branched core with at least one compound selected from the group consisting of carboxylic anhydrides and acids to form an ester bridge therewith, thereby forming an intermediate polyester macromolecule; and
  (d) reacting the intermediate polyester macromolecule with a second chain extender having a terminal or non-terminal epoxide group and a branched hydrocarbon chain, to form the wax-modified hyperbranched polyol.

9. The coating composition according to claim 8, wherein the wax-modified hyperbranched polyol is prepared by a process comprising:
  (b) further reacting the first generation branched core with the first chain extender to form a subsequent generation branched core;
  (c) reacting the subsequent generation branched core with at least one compound selected from the group consisting of carboxylic anhydrides and acids to form an ester bridge therewith, thereby forming an intermediate polyester macromolecule.

10. The coating composition according to claim 8, comprising 5% to 60% by weight of the wax-modified hyperbranched polyol based on a total amount of film-forming materials in the coating composition, and comprising no silica.

11. The coating composition according to claim 8, further comprising at least one of a hydrogen-functional resin and hydrogen-functional polymer.

12. A method for coating a substrate, comprising applying to the substrate the coating composition of claim 8 to form a coating layer, and curing the coating layer.

13. A compound of formula (I), (II), (III), or (IV):

$$E\text{-}[OC(O)ACOO\text{-}]_x\text{-}P\text{---}(\text{---}OC(O)W)_n \quad (I)$$

where:
P is a $C_3$-$C_{60}$ polyol moiety, bonded to x [OC(O)ACOO—] and n-(—OC(O)W) moieties through x+n —OH functionalities;
n is 1-2;
W is a $C_8$-$C_{60}$ linear or branched alkane moiety; x is 1-8;
A is a $C_2$-$C_{22}$ substituted or unsubstituted aliphatic, alicyclic or aromatic moiety;
and E is hydrogen or R—C(OH), where R is a substituted or unsubstituted $C_1$-$C_{22}$ aliphatic, alicyclic or aromatic moiety;
where:

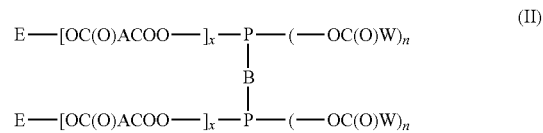

P is a $C_3$-$C_{60}$ polyol moiety, bonded to x [OCOACOO—] and n-(—OCOW) moieties through x+n —OH functionalities;
n is 1-2;
W is a $C_8$-$C_{60}$ linear or branched alkane moiety;
x is 1-8;
A is a $C_2$-$C_{22}$ substituted or unsubstituted aliphatic, alicyclic or aromatic moiety;
E is hydrogen or R—C(OH), where R is a substituted or unsubstituted $C_1$-$C_{22}$ aliphatic, alicyclic or aromatic moiety; and
B is a substituted or unsubstituted $C_4$-$C_{36}$ aliphatic, alicyclic or aromatic moiety esterified to P through a P —OH functionality;

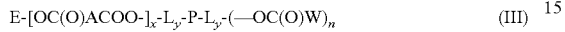  (III)

where:
P is a $C_3$-$C_{60}$ polyol moiety, bonded to x [OC(O)ACOO—] and n-(—OC(O)W) moieties through x+n —OH functionalities;
n is 1-2;
W is a $C_8$-$C_{60}$ linear or branched alkane moiety; x is 1-8;
A is a $C_2$-$C_{22}$ substituted or unsubstituted aliphatic, alicyclic or aromatic moiety;
E is hydrogen or R—C(OH), where R is a substituted or unsubstituted $C_1$-$C_{22}$ aliphatic, alicyclic or aromatic moiety; and L is a lactone moiety where y is 1-5

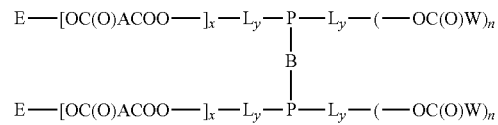  (IV)

where
P is a $C_3$-$C_{60}$ polyol moiety, bonded to x [OC(O)ACOO—] and n-(—OC(O)W) moieties through x+n —OH functionalities;
n is 1-2;
W is a $C_8$-$C_{60}$ linear or branched alkane moiety; x is 1-8;
A is a $C_2$-$C_{22}$ substituted or unsubstituted aliphatic, alicyclic or aromatic moiety;
E is hydrogen or R—C(OH), where R is a substituted or unsubstituted $C_1$-$C_{22}$ aliphatic, alicyclic or aromatic moiety;
B is a substituted or unsubstituted $C_4$-$C_{36}$ aliphatic, alicyclic or aromatic moiety esterified to P through a P —OH functionality; and
L is a lactone moiety where y is 1-5.

* * * * *